US010351577B2

(12) United States Patent
Martin et al.

(10) Patent No.: US 10,351,577 B2
(45) Date of Patent: Jul. 16, 2019

(54) ETHER ANALOGUES OF GALIELLALACTONE

(71) Applicant: Glactone Pharma Development AB, Helsingborg (SE)

(72) Inventors: Johansson Martin, Petersborough (CA); Olov Sterner, Malmö (SE); Anders Bjartell, Malmö (SE); Rebecka Hellsten, Limhamn (SE); Zilma Escobar, Lund (SE)

(73) Assignee: Glactone Pharma Development AB, Helsingborg (SE)

( * ) Notice: Subject to any disclaimer, the term of this patent is extended or adjusted under 35 U.S.C. 154(b) by 10 days.

(21) Appl. No.: 15/578,589

(22) PCT Filed: Jun. 2, 2016

(86) PCT No.: PCT/EP2016/062437
§ 371 (c)(1),
(2) Date: Nov. 30, 2017

(87) PCT Pub. No.: WO2016/193332
PCT Pub. Date: Dec. 8, 2016

(65) Prior Publication Data
US 2018/0155360 A1 Jun. 7, 2018

(30) Foreign Application Priority Data
Jun. 5, 2015 (SE) ...................................... 1550735

(51) Int. Cl.
*C07D 405/06* (2006.01)
*C07D 405/04* (2006.01)
*C07D 405/12* (2006.01)
*C07D 493/18* (2006.01)
*C07D 307/937* (2006.01)
*A61P 25/28* (2006.01)
*A61P 31/12* (2006.01)
*A61P 37/06* (2006.01)
*A61P 35/00* (2006.01)
*A61K 31/365* (2006.01)
*A61K 31/4184* (2006.01)
*A61K 31/437* (2006.01)
*A61K 31/4433* (2006.01)
*A61K 31/4439* (2006.01)
*A61K 31/497* (2006.01)
*A61K 31/5377* (2006.01)
*A61K 31/5383* (2006.01)
*C07D 519/00* (2006.01)

(52) U.S. Cl.
CPC .......... *C07D 493/18* (2013.01); *A61K 31/365* (2013.01); *A61K 31/4184* (2013.01); *A61K 31/437* (2013.01); *A61K 31/4433* (2013.01); *A61K 31/4439* (2013.01); *A61K 31/497* (2013.01); *A61K 31/5377* (2013.01); *A61K 31/5383* (2013.01); *A61P 25/28* (2018.01); *A61P 31/12* (2018.01); *A61P 35/00* (2018.01); *A61P 37/06* (2018.01); *C07D 307/937* (2013.01); *C07D 519/00* (2013.01)

(58) Field of Classification Search
CPC ... C07D 405/06; C07D 405/04; C07D 405/12

USPC ....................................... 546/284.1; 514/337
See application file for complete search history.

(56) References Cited

U.S. PATENT DOCUMENTS 6,512,007 B1    1/2003  Baumgarten et al.

FOREIGN PATENT DOCUMENTS

WO    2012010555 A1    1/2012
WO    2015132396 A1    9/2015

OTHER PUBLICATIONS

Yu et al., "Physical characterization of, etc.," PSTT, vl. 1(3), 118-127). (Year: 1998).*
Braga et al., "Making crystals from . . . " J. Royal Soc. Chem. Commun. p. 3635-3645. (Year: 2005).*
Bernstein, "Polymorphism in . . . " p. 115-118, 272. (Year: 2002).*
Davidovich et al., "Detection of polymorphism . . . " Am. Pharm. Rev. v.&(1) p. 10, 12, 14, 16, 100). (Year: 2004).*
Dean "Analytical Chem . . . " p. 10.24-10.26. (Year: 1995).*
Ivanisevic et al. "Use of X-ray . . . " Pharm. Sci. Encycl. p. 1-42. (Year: 2010).*
Seddon "Pseudopolymorph . . . " Crystal Growth & design v.4(6) p. 108 (2 pages from internet) (Year: 2004).*
Jain et al., "Polymorphism in Pharmacy", Indian Drugs 23(6) 315-329. (Year: 1986).*
Jordan "Tamoxifen . . . " Nature Rev. v.2, p. 205-213. (Year: 2003).*
Kirk-Othmer Encyclopedia of Chemical Technology, 8, pp. 95-147. (Year: 2002).*
Vippagunta et al., "Crystalline Solids", Advanced Drug Delivery Reviews 48 3-26. (Year: 2001).*

(Continued)

*Primary Examiner* — Patricia L Morris
(74) *Attorney, Agent, or Firm* — Honigman LLP; Anna M. Budde

(57) ABSTRACT

Ether analogues of galiellalactone, methods of preparing the analogues, and use of the analogues in the treatment of cancer are disclosed. The analogues are of formula (I) or (II):

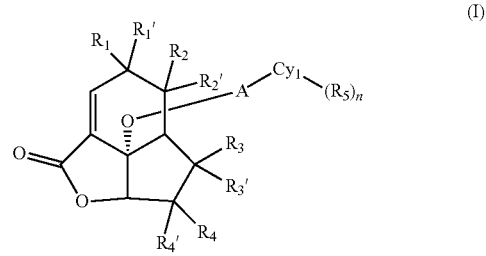

(I)

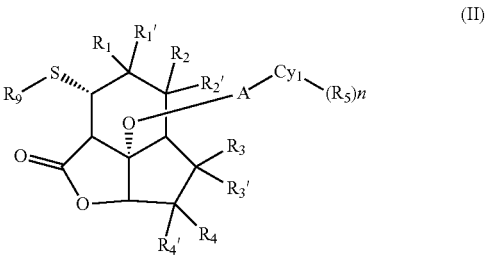

(II)

9 Claims, 2 Drawing Sheets

(56) References Cited

OTHER PUBLICATIONS

Figure 1A:
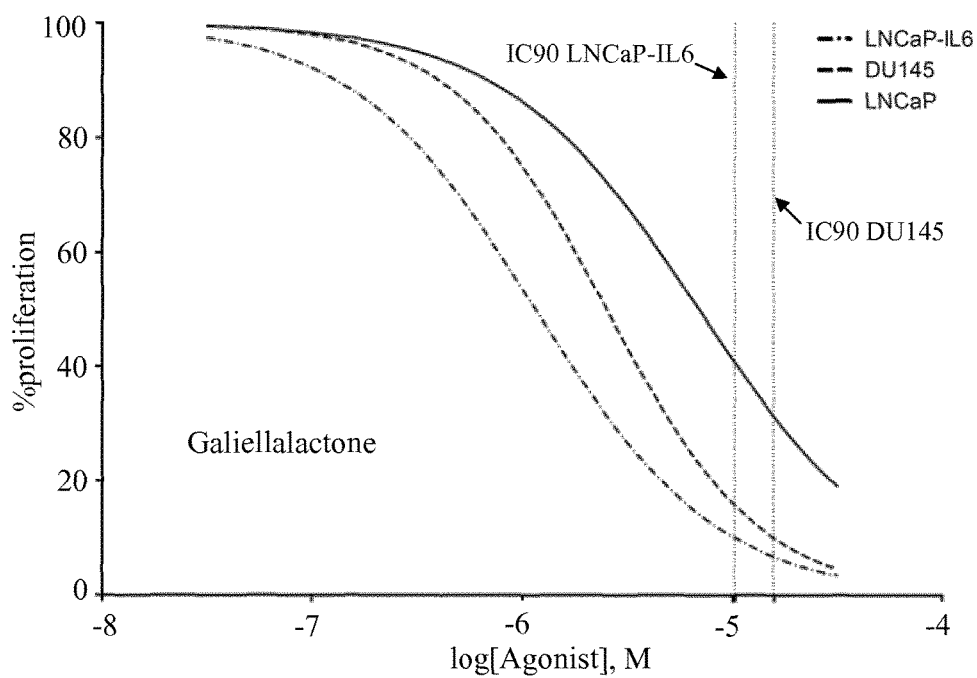

Guillory (in Brittain ed.), "Polymorphism in Pharmaceutical Solids.," NY: Marcel Dekker, Inc., 1-2, 125-181, 183-226. (Year: 1999).*

Don-Doncow et al., Targeting STAT3 in prostate cancer: Identification of STAT3 as a direct target of the fungal metabolite galiellalactone, Abstract C229, AACR-NCI-EORTC International Conference on Molecular Targets and Cancer Therapeutics, Oct. 19-23, 2013, Boston, MA.

Johnston et al., "STAT3 Signaling: Anticancer Strategies and Challenges," Molecular Interventions, Feb. 2011, pp. 18-26, vol. 11, Iss. 1, Pittsburgh, PA, USA.

Sansone et al., "Targeting the Interleukin-6/Jak/Stat Pathway in Human Malignancies," Journal of Clinical Oncology, Feb. 21, 2012, pp. 1-10, American Society of Clinical Oncology, online http://jco.ascopubs.org/cgi/doi/10.1200/JCO.2010.31.8907.

Miklossy et al., "Therapeutic Modulators of STAT Signalling for Human Diseases," Nature Reviews Drug Discovery, Aug. 2013, pp. 611-629, vol. 12, Macmillan Publishers Ltd.

Yu et al., "Revisiting STAT3 Signalling in Cancer: New and Unexpected Biological Functions," Nature Reviews Cancer, Nov. 2014, pp. 736-746, vol. 14, Macmillan Publishers Ltd.

Weidler et al., "Inhibition of Interleukin-6 Signaling by Galiellalactone," FEBS Letters, Oct. 27, 2000, pp. 1-6, vol. 484, Iss. 1, http://dx.doi.org/10.1016/S0014-5793(00)02115-3.

Hellsten et al., "Galiellalactone Is a Novel Therapeutic Candidate Against Hormone-Refractory Prostate Cancer Expressing Activated Stat3," The Prostate, 2008, pp. 269-280, vol. 68, Wiley-Liss, Inc.

Thaper et al., "New derivative of galiellalactone inhibits the STAT3 activity and suppresses ENZ-resistant Prostate Cancer in vitro," AACR Annual Meeting 2015, Abstract nr 728.

Nussbaum et al., "The High-Intrinsic Diels-Alder Reactivity of (-)-Galiellalactone; Generating Four Quaternary Carbon Centers under Mild Conditions," Eur. J. Or. Chem., 2008, pp. 2783-2790, Wiley-VCH Verlag GmbH & Co. KGaA, Weinheim.

Hausding et al., "Induction of Tolerogenic Lung CD4+ T Cells by Local Treatment with a pSTAT-3 and pSTAT-5 Inhibitor Ameliorated Experimental Allergic Asthma," International Immunology, Jan. 2011, pp. 1-15, vol. 23, No. 1, The Japanese Society for Immunology.

Don-Doncow et al., Galiellalactone Is a Direct Inhibitor of the Transcription Factor STAT3 in Prostate Cancer Cells, J. Biol. Chem. Jun. 6, 2014, vol. 289, No. 23, pp. 15969-15978.

Rudolf et al., "Inhibition of TGF-β Signaling by the Fungal Lactones (S)-Curvularin, Dehydrocurvularin, Oxacyclododecindione and Galeiellalactone," Cytokine, Jan. 2013, pp. 285-296, vol. 61, No. 1, Elsevier Ltd., USA.

Johansson, "Biosynthetic and Synthetic Studies of the Fungal Metabolite Galiellalactone," Lund Institute of Technology, 2002, Lund University, SE.

International Search Report and Written Opinion dated Aug. 8, 2016 for International Application No. PCT/EP2016/062437, filed Jun. 2, 2016.

* cited by examiner

ETHER ANALOGUES OF GALIELLALACTONE

This application is a 35 USC § 371 United States national stage application of International Application No. PCT/EP2016/062437, filed Jun. 2, 2016, which is incorporated herein by reference in its entirety, and which claims priority to Swedish Patent Application No. 1550735-3, filed Jun, 5, 2015.

TECHNICAL FIELD

The present invention relates to ether analogues of galiellalactone, pharmaceutical compositions comprising such compounds, and a method of treating or alleviating conditions, in particular cancer, by use of such compounds.

BACKGROUND

Cancer is a heterogeneous disease. A treatment should be adopted for a given type of cancer as determined by the location and genetic makeup of the tumor. However, all forms of cancer show some fundamental similarities including uncontrolled growth and self-renewal and this is in some ways driven by the pattern of gene expression. Since many different signals, regardless of cause, converge on transcription factors, and since the activation of transcription factors is a nodal point for gene transcription, transcription factors should be convergent targets for treating cancer.

Transcription factors are essential cellular components mediating different extracellular signals, including developmental and environmental, by binding to transcription responsive elements in the genome and thereby initiating the transcription of specific target genes. Aberrant transcription factor function is often associated with different diseases and leads to either increased or excessive gene transcription. As many signals and activating mechanisms converge on single transcription factors they could make efficient drug targets, e.g. for treatment of cancer.

Latent cytoplasmic transcription factors (LCTFs) are transcription factors that reside in the cytoplasm in an inactive form until they are activated through an external signal often in the form of a cell surface receptor-ligand interaction. Among these transcription factors are the family of Signal Transducer and Activator of Transcription (STAT) proteins. The STAT proteins have dual roles as they can act as both transducers of signals through the cytoplasm and function as transcription factors in the nucleus.

STAT3 is one of 6 members of the STAT family of transcriptions factors. It is an approx. 770 amino acid long protein with 6 subunits or domains; N-terminal, coiled-coil, DNA-binding, linker, SH2 and transactivation domains. STAT3 is activated by cytokine, growth factor and non-receptor mediated signaling. The canonical mechanism of STAT3 activation is kinase mediated phosphorylation of tyrosine 705 (Y705) in the SH2 domain. This triggers a reciprocal recognition of two SH2 domains of STAT3 monomers leading to the formation of a STAT3 dimer. This dimer is translocated to the nucleus, aided by importins, and transcription of target genes, through binding to DNA, is activated. On its way to the nucleus STAT3 can be further modified through serine phosphorylation, lysine acetylation or Small Ubiquitin-like Modifier (SUMO) protein attachment and these modifications serve to modulate the transcriptional activity of STAT3

STAT3 activation and dimerization through phosphorylation can be achieved through at least three responses. STAT3 can be phosphorylated by JAK kinases that are constitutively bound to cytokine receptors. Upon ligand binding, the receptors aggregate and the JAK2 proteins undergo reciprocal activation through phosphorylation and they can then recruit and activate STAT3 through binding to the SH2 domain. Alternatively growth factor receptors can directly recruit and associate with STAT3 leading to STAT3 activation through their receptor tyrosine kinase activity. Finally, non-receptor kinases, e.g. Src family kinases and Abl, can also activate STAT3. In addition non-phosphorylated STAT3 can be transported into the nucleus and participate in transcription probably by binding to other proteins to form functional heteromeric transcription factors.

In the nucleus STAT3 can interact with several other proteins including other transcription factors e.g. NF-κB.

STAT3 can also be activated by phosphorylation on serine 727 by various kinases. This phosphorylation leads to enhanced transcriptional activity. Constitutively phosphorylated serine 727 is widespread in cells from patients suffering from chronic lymphocytic leukemia (CLL).

Since STAT3 activation under normal conditions is transient, multiple negative feedback systems exist. STAT3 signaling is tightly regulated and it is not constitutively activated in normal tissue. Several endogenous negative regulators for STAT3 signaling have been found and these include Suppressor of cytokine signaling (SOCS, that bind to and inactivate JAKs) and protein inhibitor of activated STAT (PIAS). SOCS is also a gene product of STAT3 transcription demonstrating this as a negative feedback loop. Loss of PIAS or SOCS function or reduced expression will increase STAT3 activation and mutations of these regulatory factors have been found in diseases related to increase STAT3 signaling.

Finally STAT3 is dephosphorylated in the nucleus by different phosphatases and the dephophorylated STAT3 monomers are transported out of the nucleus where they once again reside latent.

The target genes of STAT3 transcription are involved in cell growth and cell cycle regulation (e.g. Cyclin Dl, c-Myc, p27), apoptosis (e.g. Mcl-1, survivin, Bcl-2, and Bcl-xL), angiogenesis (VEGF) and metastasis (e.g. MMP-2, MMP-3).

STAT3 can be activated by cytokines and growth factors including IL6, LIF, IL-10, IL-1, IL-12, EGF, TGFalpha, PDGF and G-CSF and various tyrosine and serine kinases including JAK, JAK2, JAK3, TYK2, Src, Src, Lck, Hck, Lyn, Fyn, Fgr, EGFR, ErbB-2, Grb2, JNK, P38MAPK and ERK.

STAT3 is an experimentally validated target in several cancer forms, including leukemia, lymphomas, multiple myeloma, breast cancer, prostate carcinoma, lung cancer (non-small-cell), renal cell carcinoma lung cancer, hepatocellular carcinoma, cholangiocarcinoma, ovarian carcinoma, pancreatic adenocarcinoma, melanoma, head and neck squamous cell carcinoma (Johnston, P. A; Grandis, J. R. Mol Interv. 2011 11(1): 18-26). STAT3 signaling is involved in proliferation, survival, metastasis, drug resistance and migration of cancer cells and it also links inflammation and cancer. This has been demonstrated in numerous studies in vitro, using primary cells or immortalized cell lines, or in vivo using xenograft models (cf. e.g. Sansone, P; Bromberg, J. J Clin Oncol. 2012; 30(9):1005-14, and Miklossy, G.; Hilliard, T. S.; Turkson, J. Nat Rev Drug Discov. 2013 12(8):611-29) and as such is believed to be an ideal target for cancer therapy (Yu, H.; Lee, H.; Herrmann, A.; Buettner, R.; Jove, R. Nat Rev Cancer. 2014 14(11):736-46.

The sensitivity of many cancer cell lines to STAT3 inhibition indicates an oncogene signaling dependence.

Inflammation and immunity are also important parts of cancer etiology. Cancer cells can promote inflammation in the tumor microenvironment and avoid the innate immune system. STAT3 signaling plays an important dual role in this process. STAT3 is activated by pro-inflammatory cytokine signaling and STAT3 activation opposes T-helper cell antitumor responses. Ablation of STAT3 signaling leads to a potent immunological antitumor response. STAT3 is more activated in tumor infiltrating immune cells than in normal tissue and targeting STAT3 causes therapeutic antitumor immunity.

In summary aberrant and deregulated STAT3 promotes cell proliferation and cell survival in both solid and hematological tumors, including breast, lung, brain, colon, prostate, lymphoma and leukemia. Direct inhibitors of STAT3 or inhibitors of STAT3 signaling are thus deemed to be able to mitigate or cure those pathological states.

The treatments for prevention, revocation or reduction of diseases like e.g. cancer are in many ways insufficient. Hence, compounds effective in modulating or inhibiting the above described STAT signaling would be desired.

The direct inhibition of STAT3 can be achieved by inhibiting the protein-protein interaction involved in STAT3 dimerization (STAT3 is a dimer of two proteins) or by blocking the protein-DNA interaction required for STAT3 binding to DNA for the initiation of transcription. Alternatively the production (biosynthesis) of STAT3 can be blocked.

The alternative to direct STAT3 inhibition is to inhibit upstream molecules in the signaling cascade responsible for STAT3 activation (e.g. the JAK kinases). The drawback with this approach is that there are multiple ways to activate STAT3.

The STAT3 SH2 has been targeted with peptidomimetics and non-peptide small molecules (e.g. S3I-M2001) to block STAT3-STAT3 dimerization and DNA binding has been blocked with oligodeoxynucleotide decoys while the production of STAT3 has been inhibited by antisense.

STAT1 is also a member of the STAT family and STAT1 is activated by either type I, type II, or type III interferon stimulation and is involved in upregulating genes that primarily are involved in controlling the growth and apoptosis of immune cells. In response to IFN-γ stimulation, STAT1 forms homodimers, or heterodimers with STAT3, that bind to the Interferon-Gamma-Activated Sequence (GAS) promoter element leading to an increased expression of Interferon-Stimulated Genes (ISG). Intact STAT1 signalling is important for the immune defense against viral and bacterial infections.

Transcription factors such as STAT3 that are disregulated in cancer and other illnesses are important targets for potential drugs but the numerous roles played by other transcription factors in healthy cells makes it important to attain transcription factor blocking drugs with a high degree of selectivity and since many transcription factors have similar activation modes and structural similarities this can be difficult to achieve.

(−)-Galiellalactone is a natural product isolated from wood-inhabiting fungi with submicromolar inhibition of IL-6/STAT3 signaling.

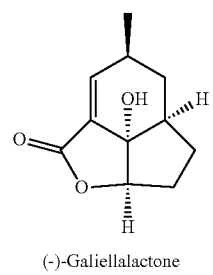

(−)-Galiellalactone

In U.S. Pat. No. 6,512,007 use of galiella lactone as a pharmaceutical for the treatment of e.g. inflammatory processes is disclosed.

The biological effect of (−)-galiellalactone seemingly is due to a direct inhibition of the binding of STAT3-dimers to their regulatory elements (Weidler et al in FEBS Letters 2000, 484, 1-6). Based on this proposed mechanism of action, galiellalactone has been evaluated as an anti-cancer agent. Hellsten et al reported in *Prostate* 68:269-280 (2008) that galiellalactone inhibits the proliferation of STAT3 expressing DU145 prostate cancer cells. Further, Hellsten et al ("*Targeting STAT3 in prostate cancer: Identification of STAT3 as a direct target of the fungal metabolite galiellalactone*" Nicholas Don-Doncow, Zilma Escobar, Martin Johansson, Eduardo Muñoz, Olov Sterner, Anders Bjartell, Rebecka Hellsten, AACR-NCI-EORTC International Conference on Molecular Targets and Cancer Therapeutics, Oct. 19-23, 2013, Boston, Mass. Abstract nr C229; Don-Doncow, N.; Escobar, Z.; Johansson, M.; Kjellström, S.; Garcia, V.; Munoz, E.; Sterner, O.; Bjartell, A.; Hellsten, R.; *J. Biol. Chem.* 2014 289(23):15969-78) have shown that galiellalactone binds directly and covalently to STAT3, thus inhibiting the transcriptional activity. Galiellalactone is thus a candidate drug for treatment of cancer. Also Thaper et al ("*GPA500 inhibits the STAT3 activity and suppresses ENZ-resistant Prostate Cancer in vitro*". Daksh Thaper, Sepideh Vahid, Jennifer Bishop, Martin Johansson and Amina Zoubeidi. AACR Annual Meeting 2015, Abstract nr 728) showed that galiellalactone can block STAT3 activity in enzalutamide resistant cells which leads to decreased proliferation and PSA production.

Galiellalactone also inhibits STAT1. Further, galiellalactone reduces the proliferation of non-STAT3 driven prostate cancer cells known as LNCaP cells. This clearly indicates that galiellalactone has off-target effects. As STAT1 signalling is believed to have an anti-oncogenic role in cells it would be desirable to obtain galiellalactone-based STAT3 inhibitors that have reduced STAT1 inhibitory properties. It would also be desirable to increase the anti-proliferative selectivity towards STAT3 driven cells in order to more specifically target STAT3 dependent cells.

Attempts to modify the activity and properties of galiellalactone have been reported in the art. Nussbaum et al reported in Eur. J. Org. Chem. 2004, 2783-2790 on the modification of individual functional groups of (−)-galiellalactone. Most of the resulting analogues, however, turned out to be completely inactive or much less active than (−)-galiellalactone. Especially, modifications of the conjugated double bond were reported to produce inactive compounds. WO 2012/010555 discloses the preparation and use of tricylic compounds based on a galiellalactone scaffold that inhibit STAT3 and NF-kB signaling.

5

Nevertheless, there remains a need for more selective inhibitors of STAT3 based on galiellalactone.

SUMMARY

The present invention seeks to mitigate, alleviate, circumvent or eliminate at least one, such as one or more, of the above-identified deficiencies by providing a compound, according to an aspect, a compound according to formula (I)

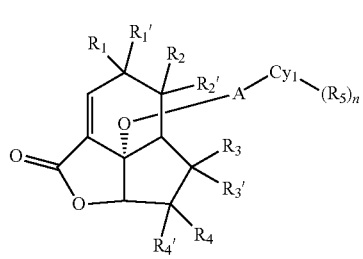

wherein $R_1$ and $R_1'$ are independently selected from the group consisting of H, C1-5 alkyl, C1-5 fluoroalkyl, halo, cyano, nitro, —OH, OC1-5 alkyl, C1-5 alkyleneOH, C1-5 alkyleneOC1-5 alkyl, C3-8 non-aromatic carbocycle, OC1-5 fluoroalkyl, C1-3 alkyleneOC1-5 fluoroalkyl, OC(O)C1-5 alkyl, C1-3 alkyleneOC(O)C1-5 alkyl, OC2-3 alkyleneNH$_2$, OC2-3 alkyleneNH(C1-5 alkyl), OC2-3 alkyleneN(C1-5 alkyl)$_2$ in which the C1-5 alkyl may be the same or different, —NH$_2$, —NH(C1-5 alkyl), C1-3 alkyleneNH$_2$, C1-3 alkyleneNH(C1-5 alkyl), —N(C1-5 alkyl)$_2$ in which the C1-5 alkyl may be the same or different, C1-3 alkyleneN(C1-5 alkyl)$_2$ in which the C1-5 alkyl may be the same or different, NHC(O)C1-5 alkyl, N(C1-5 alkyl)C(O)C1-5 alkyl, C1-3 alkyleneNHC(O)C1-5 alkyl, C1-3 alkyleneN(C1-5 alkyl)C(O)C1-5 alkyl, NHaryl, C1-3 alkyleneNHaryl, wherein the aryl is unsubstituted or substituted with one or more substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, NH2, NH(C1-5 alkyl), and N(C1-5 alkyl)$_2$ in which the C1-5 alkyl may be the same or different, NHheteroaryl, C1-3 alkyleneNHheteroaryl, wherein said heteroaryl is a 5- or 6-membered heteroaryl, said heteroaryl being unsubstituted or substituted with a one or several independently selected from C1-5 alkyl, C(O)NH$_2$, C(O)NHC1-5 alkyl, C1-3 alkyleneC(O)NH$_2$, C1-3 alkyleneC(O)NHC1-5 alkyl, C(O)N(C1-5 alkyl)$_2$ in which the C1-5 alkyl may be the same or different, C1-3 alkyleneC(O)N(C1-5 alkyl)$_2$ in which the C1-5 alkyl may be the same or different, C(O)N(C4-5 alkylene), C1-3 alkyleneC(O)N(C4-5 alkylene), C(O)OH, C(O)OC1-5 alkyl, C1-3 alkyleneC(O)OH, C1-3 alkyleneC(O)OC1-5 alkyl, and a 3- to 8-membered non-aromatic heterocycle, aryl, C1-3 alkylene-aryl, wherein the aryl is unsubstituted or substituted with one or several substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, —NH$_2$, —NH(C1-5 alkyl), and N(C1-5 alkyl)$_2$ in which the C1-5 alkyl may be the same or different, heteroaryl, C1-3 alkylene-heteroaryl, wherein said heteroaryl is a 5- or 6-membered heteroaryl, said heteroaryl

6 being unsubstituted or substituted with one or several independently selected C1-5 alkyl groups, halo, cyano, —CH$_2$-cyano, —SH, SC1-5 alkyl, SO$_2$H, SO$_2$C1-5 alkyl, C1-3 alkyleneSO$_2$H, C1-3 alkyleneSO$_2$C1-5 alkyl, nitro, C(O)H, C(O)C1-C5 alkyl, C(O)C1-C5 fluoroalkyl, NHSO$_2$C1-C5 alkyl, N(C1-C3 alkyl)SO$_2$C1-C5 alkyl, NHSO$_2$C1-5 fluoroalkyl, and N(C1-C5 alkyl)SO$_2$C1-5 fluoroalkyl, —SH, —SC1-5 alkyl, C1-5 alkylene-SH, C1-5 alkylene-SC1-5 alkyl, SC1-5 fluoroalkyl, C1-5 alkyleneSC1-5 fluoroalkyl, SO2C1-5 alkyl, C1-5 alkylene-SO2C1-5 alkyl, SO2C1-5 fluoroalkyl, C1-5 alkylene-SO2C1-5 fluoroalkyl, SO$_2$NH$_2$, SO$_2$NH(C1-5 alkyl), SO$_2$N(C1-5 alkyl)$_2$ in which the C1-5 alkyl may be the same or different, C1-5 alkyleneSO$_2$NH$_2$, C1-5 alkyleneSO$_2$NH(C1-5 alkyl), C1-5 alkyleneSO$_2$N(C1-5 alkyl)$_2$ in which the C1-5 alkyl may be the same or different, SO2NHaryl, C1-5 alkyleneSO2NHaryl, wherein the aryl is unsubstituted or substituted with a one or several substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, —NH$_2$, —NH(C1-5 alkyl), and N(C1-5 alkyl)$_2$ in which the C1-5 alkyl may be the same or different, SO2N(C1-5 alkyl)aryl, and C1-5 alkyleneSO2N(C1-5 alkyl)aryl, wherein the aryl is unsubstituted or substituted with a one or several substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, —NH$_2$, —NH(C1-5 alkyl), and N(C1-5 alkyl)$_2$ in which the C1-5 alkyl may be the same or different;

$R_2$, $R_2'$, $R_3$, and $R_3'$ are each independently selected from the group consisting of H, halo, —OH, C1-5 alkyl, and C1-5 fluoroalkyl;

$R_4$ and $R_4'$ are independently selected from the group consisting of H, C1-5 alkyl, aryl, and CH$_2$aryl;

A is selected from the group consisting of a bond, C1-C5 alkylene or NR$_{10}$;

$R_{10}$ is H or C1-C3 alkyl;

$Cy_1$ is a ring selected from the group consisting of aryl, heteroaryl, a non-aromatic carbocycle, and a non-aromatic heterocycle;

$R_5$ is independently selected from the group consisting of C1-8 alkyl, C1-5 haloalkyl, halo, cyano, —CH$_2$-cyano, —OH, OC1-5 alkyl, C1-8 alkyleneOC1-5 alkyl, O-aryl, C1-8 alkylene-O-aryl, —SH, SC1-5 alkyl, SO$_2$H, SO$_2$C1-5 alkyl, C1-3 alkyleneSO$_2$H, C1-3 alkyleneSO$_2$C1-5 alkyl, OC1-3 fluroalkyl, C1-3 alkyleneOC1-3 fluroalkyl, NH2, NH(C1-3 alkyl), C1-3 alkylene-NH2, C1-3 alkyleneNH(C1-3 alkyl), N(C1-5 alkyl)$_2$ in which the C1-5 alkyl may be the same or different, C1-3 alkyleneN(C1-5 alkyl)$_2$ in which the C1-5 alkyl may be the same or different, C(O)OH, C(O)OC1-5 alkyl, C1-3 alkyleneC(O)OH, C1-3 alkyleneC(O)OC1-5 alkyl, OC(O)H, OC(O)C1-5 alkyl, C1-3 alkyleneOC(O)H, C1-3 alkyleneOC(O)C1-5 alkyl, NHC(O)H, NHC(O)C1-5 alkyl, N(C1-3 alkyl)C(O)H, N(C1-3 alkyl)C(O)C1-5 alkyl, C1-3 alkyleneNHC(O)H, C1-3 alkyleneNHC(O)C1-5 alkyl, C1-3 alkyleneN(C1-3 alkyl)C(O)H, C1-3 alkyleneN(C1-3 alkyl)C(O)C1-5 alkyl, C(O)NH2, C(O)NH(C1-3 alkyl), C1-3 alkyleneC(O)NH2, C1-3 alkyleneC(O)NH(C1-3 alkyl), C(O)N(C1-5 alkyl)$_2$, in which the C1-5 alkyl may be the same or different, C1-3 alkyleneC(O)N(C1-5 alkyl)$_2$, in which the C1-5 alkyl may be the same or different, nitro, C(O)H, C(O)C1-C5 alkyl, NHSO2C1-C5 alkyl, N(C1-C3 alkyl)SO2C1-C3 alkyl, NHSO2C1-C3 fluoroalkyl, N(C1-C3 alkyl)SO2C1-C3 fluoroalkyl, OC2-

C3alkyleneNH2, OC2-C3alkyleneNH(C1-C3 alkyl), OC2-C3alkyleneN(C1-C3 alkyl)$_2$ in which the C1-3 alkyl may be the same or different, and

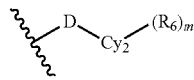

wherein

D is selected from the group consisting of a bond, C1-3 alkylene, O—C1-3 alkylene, C1-3 alkylene-O—C1-3 alkylene, OC(O)C1-3 alkylene, C1-3 alkylene-OC(O)—C1-3 alkylene, C(O)OC1-3 alkylene, C1-3 alkylene-C(O)O—C1-3 alkylene, C(O)N(H)(C1-3 alkylene), C(O)N(C1-3 alkyl)(C1-3 alkylene), C1-3 alkylene-C(O)N(H)(C1-3 alkylene), C1-3 alkylene-C(O)N(C1-3 alkyl)(C1-3 alkylene), N(H)C(O)C1-3 alkylene, N(C1-3 alkyl)C(O)C1-3 alkylene, C1-3 alkylene-N(H)C(O)C1-3 alkylene, C1-3 alkylene-N(C1-3 alkyl)C(O)C1-3 alkylene, —NHSO2-, —SO2NH—, SO2, SO, C(O), C1-3 alkylene-C(O), C(O)C1-3 alkylene, C1-3 alkylene C(O)C1-3 alkylene, NH, N(C1-3 alkyl), NH—C1-3 alkylene, N(C1-3 alkyl)-C1-3 alkylene, C1-3 alkylene-NH, C1-3 alkylene-N(C1-3 alkyl), C1-3 alkylene-NH—C1-3 alkylene, C1-3 alkylene-N(C1-3 alkyl)-C1-3 alkylene, and S;

Cy2 is a 5-membered heteroaryl, a 6-membered heteroaryl, phenyl, a 3- to 8-membered non-aromatic heterocycle or a C3-8 non-aromatic carbocycle;

m is an integer selected from the group consisting of 0, 1, 2, 3, 4, and 5;

$R_6$ is independently selected from oxo, C1-5 alkyl, C1-5 fluoroalkyl, halo, cyano, —CH$_2$-cyano, —OH, OC1-5 alkyl, C1-5 alkylene-OH, C1-5 alkyleneOC1-5 alkyl, —SH, SC1-5 alkyl, SO2H, SO2C1-5 alkyl, C1-3 alkyleneSO2H, C1-3 alkyleneSO2C1-5 alkyl, OC1-3 fluoroalkyl, C1-3 alkyleneOC1-3 fluoroalkyl, NH2, NH(C1-3 alkyl), C1-3 alkylene-NH2, C1-3 alkylene-NH(C1-3 alkyl), N(C1-5 alkyl)2 in which the C1-5 alkyl may be the same or different, C1-3 alkyleneN(C1-5 alkyl)2 in which the C1-5 alkyl may be the same or different, C(O)OH, C(O)OC1-5 alkyl, C1-3 alkylene-C(O)OH, C1-3 alkylene-C(O)OC1-5 alkyl, OC(O) H, OC(O)C1-5 alkyl, C1-3 alkylene-OC(O)H, C1-3 alkylene-OC(O)C1-5 alkyl, NHC(O)H, NHC(O)C1-3 alkyl, N(C1-3 alkyl)C(O)H, N(C1-3 alkyl)C(O)C1-3 alkyl, C1-3 alkylene-NHC(O)H, C1-3 alkylene-NHC(O)C1-3 alkyl, C1-3 alkylene-N(C1-3 alkyl)C(O)H, C1-3 alkylene-N(C1-3 alkyl)C(O)C1-3 alkyl, C(O)NH2, C(O)NH(C1-3 alkyl), C1-3 alkylene-C(O)NH2, C1-3 alkylene-C(O)NH(C1-3 alkyl), C(O)N(C1-5 alkyl)2 in which the C1-5 alkyl may be the same or different, C1-3 alkyleneC(O)N(C1-5 alkyl)2 in which the C1-5 alkyl may be the same or different, C(O)N (C4-5 alkylene), C1-3 alkyleneC(O)N(C4-5 alkylene), nitro, C(O)H, C(O)C1-C5 alkyl, C(O)C1-C3 fluoroalkyl, NHSO$_2$C1-C3 alkyl, N(C1-C3 alkyl)SO$_2$C1-C3 alkyl, NHSO$_2$C1-C3 fluoroalkyl, N(C1-C3 alkyl)SO$_2$C1-C3 fluoroalkyl, OC2-C3 alkyleneNH$_2$, OC2-C3 alkyleneNH(C1-C3 alkyl), and OC2-C3 alkyleneN(C1-C3 alkyl)2 in which the C1-3 alkyl may be the same or different; or when two R6 are present, each R6 is combined to form a fused ring or spiro ring with Cy2;

n is an integer selected from the group consisting of 0, 1, and 2;

as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

Another aspect disclosed herein relates to a compound according to formula (II)

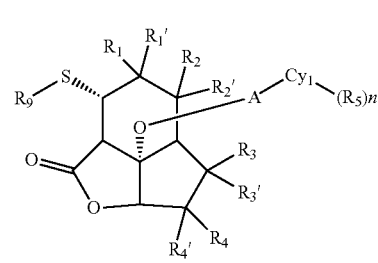

wherein $R_1$, $R_{1'}$, $R_2$, $R_{2'}$, $R_3$, $R_{3'}$, $R_4$, $R_{4'}$, A, Cy$_1$, $R_5$, and n are defined as above in respect of compounds of formula (I);

R9 is a moiety according to formula (III),

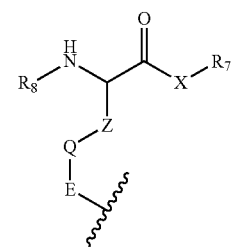

wherein the waved line indicates the point of attachment to the sulfur atom in formula (II);

Z is a C1-5 alkylene;

Q is a bond, a phenylene, or a heteroarylene, wherein said heteroarylene is a 5- or 6-membered heteroarylene;

E is a bond or a C1-5 alkylene;

X is selected from the group consisting of NH, NC1-C5 alkyl or "O" (oxygen);

R7 is selected from the group consisting of H, C1-C10 alkyl, C1-5 alkyleneN(C1-5 alkyl)$_2$ in which the C1-5 alkyl may be the same or different, aryl, C1-3 alkylene-aryl wherein the aryl is unsubstituted or substituted with a one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, nitro, cyano, NH$_2$, NH(C1-5 alkyl), and N(C1-5 alkyl)$_2$ in which the C1-5 alkyl may be the same or different, C1-3 alkylene heteroaryl, wherein said heteroaryl is a 5- or 6-membered heteroaryl, said heteroaryl being unsubstituted or substituted with a one or several independently selected C1-5 alkyl groups, an amino acid residue selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (III) at the N-terminal of the amino acid residue and optionally esterfied at the C-terminal with a C1-5 monohydric alkanol, and a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (III) at the N-terminal of the peptide and optionally esterfied at the C-terminal with a C1-5 monohydric alkanol;

provided that R7 cannot be H if X is "O" (oxygen); and
R8 is selected from the group consisting of:
C(O)C1-C6 alkyl, C(O)OC1-C6 alkyl,
C(O)-aryl, C(O)C1-3 alkylene-aryl wherein the aryl is unsubstituted or substituted with a one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, nitro, cyano, $NH_2$, NH(C1-5 alkyl), and N(C1-5 alkyl)$_2$ in which the C1-5 alkyl may be the same or different,
C(O)-heteroaryl, C(O)C1-3 alkylene-heteroaryl wherein said heteroaryl is a 5- or 6-membered heteroaryl, said heteroaryl being unsubstituted or substituted with one or several independently selected C1-5 alkyl groups, an amino acid residue selected from the group consisting of alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (III) at the C-terminal of the amino acid residue, and which amino acid residue is optionally N-acylated, wherein said acyl group is selected from the group consisting C(O)C1-C6 alkyl, C(O)-aryl, and C(O)C1-3 alkylene-aryl, wherein the aryl is unsubstituted or substituted with a one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, nitro, cyano, $NH_2$, NH(C1-5 alkyl), and N(C1-5 alkyl)$_2$ in which the C1-5 alkyl may be the same or different, and
a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (III) at the C-terminal of the peptide, and the N-terminal of the peptide optionally being N-acelyated, wherein said acyl group is selected from the group consisting C(O)C1-C6 alkyl, C(O)-aryl, and C(O)C1-3 alkylene-aryl, wherein the aryl is unsubstituted or substituted with a one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, nitro, cyano, $NH_2$, NH(C1-5 alkyl), and N(C1-5 alkyl)$_2$ in which the C1-5 alkyl may be the same or different;

as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

According to another aspect, there is provided a pharmaceutical composition comprising a compound according to formula (I) or formula (II) and at least one pharmaceutically acceptable carrier or excipient. Such compound and composition are useful in therapy.

According to another aspect, compounds according to formula (I) or formula (II) and compositions comprising such compounds are useful in the treatment of STAT3 signaling related disorders as well as in treatment of diseases and disorders selected from the group consisting of: solid cancers, hematological cancers, benign tumors, hyperproliferative diseases, inflammations, autoimmune diseases, graft or transplant rejections, delayed physiological function of grafts or transplants, neurodegenerative diseases and viral infections, such as from solid cancers and hematological cancers.

According to another aspect, there is provided a use of a tertiary amine in the reaction of an unsubstituted or substituted galiellalactone-O-LG with an alcohol to form an unsubstituted or substituted galiellalactone ether, wherein LG is a leaving group.

Further, advantageous features of various embodiments of the invention are defined in the dependent claims and within the detailed description below.

DETAILED DESCRIPTION OF EMBODIMENTS

Definitions

Unless defined otherwise, all technical and scientific terms used herein have the same meaning as is commonly understood by one of ordinary skill in the art.

In the context of the present application and invention, the following definitions apply:

The term "addition salt" is intended to mean salts formed by the addition of a pharmaceutical acceptable acid, such as organic or inorganic acids, or a pharmaceutical acceptable base. The organic acid may be, but is not limited to, acetic, propanoic, methanesulfonic, benzenesulfonic, lactic, malic, citric, tartaric, succinic or maleic acid. The inorganic acid may be, but is not limited to, hydrochloric, hydrobromic, sulfuric, nitric acid or phosphoric acid. The base may be, but is not limited to, ammonia and hydroxides of alkali or alkaline earth metals. The term "addition salt" also comprises the hydrates and solvent addition forms, such as hydrates and alcoholates.

As used herein, "halo" or "halogen" refers to fluoro, chloro, bromo, and iodo.

As used herein, "alkyl" used alone or as a suffix or prefix, is intended to include both branched and straight chain saturated aliphatic hydrocarbon groups having from 1 to 12 carbon atoms or if a specified number of carbon atoms is provided then that specific number is intended. For example "C1-6 alkyl" denotes alkyl having 1, 2, 3, 4, 5 or 6 carbon atoms. Examples of alkyl include, but are not limited to, methyl, ethyl, n-propyl, i-propyl, n-butyl, i-butyl, sec-butyl, t-butyl, pentyl, and hexyl.

As used herein, "alkylenyl" or "alkylene" used alone or as a suffix or prefix, is intended to include straight chain saturated aliphatic hydrocarbon groups having from 1 to 12 carbon atoms or if a specified number of carbon atoms is provided then that specific number is intended. For example "C1-6 alkylenyl" or "C1-6 alkylene" denotes alkylenyl or alkylene having 1, 2, 3, 4, 5 or 6 carbon atoms. As used herein, the groups linked by an alkylene or alkylenyl group are intended to be attached to the first and to the last carbon of the alkylene or alkylenyl-group. In the case of methylene, the first and the last carbon is the same. For example, "H₂N(C2 alkylene)NH₂", "H₂N(C3 alkylene)NH₂", "N(C4 alkylene)", "N(C5 alkylene)" and "N(C2 alkylene)₂NH" are equivalent to 1,2-diamino ethane, 1,3-diamino propane, pyrrolidinyl, piperidinyl and piperazinyl, respectively. The combination "N(C4-5 alkylene)" refers to pyrrolidinyl and piperidinyl. Examples of alkylene or alkylenyl include, but are not limited to, methylene (—CH₂—), ethylene (—CH2CH₂—), propylene (—CH₂CH₂CH₂—), and butylene (—CH₂CH₂CH₂CH₂—).

As used herein, "alkoxy" or "alkyloxy" is intended to mean an alkyl group as defined above with the indicated number of carbon atoms attached through an oxygen bridge. Examples of alkoxy include, but are not limited to, methoxy, ethoxy, n-propoxy, isopropoxy, n-butoxy, isobutoxy, t-butoxy, n-pentoxy, isopentoxy, cyclopropylmethoxy, allyloxy and propargyloxy. Similarly, "alkylthio" or "thioalkoxy" represent an alkyl group as defined above with the indicated number of carbon atoms attached through a sulphur bridge.

As used herein, "fluoroalkyl", "fluoroalkylene" and "fluoroalkoxy", used alone or as a suffix or prefix, refers to groups in which one, two, or three of the hydrogen(s) attached to any of the carbons of the corresponding alkyl, alkylene and alkoxy-groups are replaced by fluoro.

Examples of fluoroalkyl include, but are not limited to, trifluoromethyl, difluoromethyl, fluoromethyl, 2,2,2-trifluoroethyl, 2-fluoroethyl and 3-fluoropropyl.

Examples of fluoroalkylene include, but are not limited to, difluoromethylene, fluoromethylene, 2,2-difluorobutylene and 2,2,3-trifluorobutylene.

Examples of fluoroalkoxy include, but are not limited to, trifluoromethoxy, 2,2,2-trifluoroethoxy, 3,3,3-trifluoropropoxy and 2,2-difluoropropoxy.

As used herein, "non-aromatic carbocycle", whether alone or as a suffix or prefix, is intended to mean non-aromatic saturated and unsaturated carbomonocycles, having from 3 to 8 ring carbon atoms, such as cyclopropanyl, cyclopentanyl, cyclohexanyl, cyclopentenyl and cyclohexenyl. If a prefix, such as C3-C6, is given, when said carbocycle comprises the indicated number of carbon atoms, eg. 3, 4, 5 or 6 carbon atoms. Accordingly, "C6 non-aromatic carbocycle" for example includes cyclohexyl and cyclohexenyl. Non-aromatic unsaturated carbocycles are to be distinguished from aryls, as aryl refers to aromatic ring structures, comprising at least one aromatic ring.

As used herein, "cycloalkyl", whether alone or as a suffix or prefix, is intended to mean a saturated carbomonocycle, having from 3 to 8 ring carbon atoms, such as cyclopropanyl, cyclopentanyl and cyclohexanyl. If a prefix, such as C3-C6, is given, when said cycloalkyl comprises the indicated number of carbon atoms, e.g. 3, 4, 5 or 6 carbon atoms. Accordingly, C6 cycloalkyl corresponds to cyclohexyl.

As used herein, "cycloalkenyl", whether alone or as a suffix or prefix, is intended to mean a monounsaturated carbomonocycle, having from 4 to 8 ring carbon atoms, such as cyclopentenyl and cyclohexenyl. If a prefix, such as C3-C6, is given, when said cycloalkenyl comprises the indicated number of carbon atoms, eg. 3, 4, 5, or 6 carbon atoms. Accordingly, C6 cycloalkenyl corresponds to cyclohexenyl.

As used herein, the term "substitutable" refers to an atom to which hydrogen may be covalently attached, and to which another substituent may be present instead of the hydrogen. A non-limiting example of substitutable atoms includes the carbon-atoms of pyridine. The nitrogen-atom of pyridine is not substitutable according to this definition. Further, according to the same definition, the imine nitrogen at position 3 in imidazole is not substitutable, while the amine nitrogen at position 1 is.

As used herein, the term "aryl" refers to a ring structure, comprising at least one aromatic ring, made up of from 5 to 14 carbon atoms. Ring structures containing 5, 6, or 7 carbon atoms would be single-ring aromatic groups, for example phenyl. Ring structures containing 8, 9, 10, 11, 12, 13, or 14 carbon atoms would be polycyclic, for example naphthyl. The aromatic ring may be substituted at one or more ring positions. The term "aryl" also includes polycyclic ring systems having two or more cyclic rings in which two or more carbons are common to two adjoining rings (the rings are "fused rings") wherein at least one of the rings is aromatic, for example, the other cyclic rings may be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, "heteroaryl" or "hetaryl" refers to an aromatic heterocycle, having at least one ring with aromatic character, (e.g. 6 delocalized electrons) or at least two conjugated rings with aromatic character, (e.g. 4n+2 delocalized electrons where "n" is an integer), and comprising up to about 14 carbon atoms, and having at least one heteroatom ring member such as sulfur, oxygen, or nitrogen. Heteroaryl or hetaryl groups include monocyclic and bicyclic (e.g., having 2 fused rings) systems. The aromatic ring of the heteroaryl or hetaryl group may be substituted at one or more ring positions.

Examples of heteroaryl or hetaryl groups include without limitation, pyridyl (i.e., pyridinyl), pyrimidinyl, pyrazinyl, pyridazinyl, triazinyl, furyl (i.e. furanyl), quinolyl, tetrahydroquinolyl, isoquinolyl, tetrahydroisoquinolyl, thienyl, imidazolyl, thiazolyl, indolyl, pyrrolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, benzimidazolyl, indolinyl, and the like.

As used herein, "non-aromatic heterocycle" refers to a monocycle comprising at least one heteroatom ring member, such as sulfur, oxygen, or nitrogen. Such monocyclic rings may be saturated or unsaturated. If unsaturated, the non-aromatic heterocycle may contain one, two or three double bonds or one or two triple bonds. However, non-aromatic heterocycles are to be distinguished from heteroaryl groups.

Examples of non-aromatic heterocycle groups include without limitation azepinyl, dioxolanyl, imidazolinyl, pyrazolidinyl, morpholinyl, piperazinyl, 3H-diazirin-3-yl, oxiranyl, aziridinyl, piperidinyl, piperidinyl-N-oxide, pyrrolidinyl, tetrahydrofuranyl, tetrahydropyranyl, dihydro-2H-pyranyl, tetrahydrothiofuranyl, thiamorpholinyl.

An "oxo" group refers to a "=O" group.

As used herein, the term "relative stereochemistry", such as when e.g. referring to e.g. a drawing of a structure, is relating to the relative spatial arrangement of e.g. substituents or groups of a structure. For example, if the relative stereochemistry is indicated by drawing substituents or groups of a molecule in certain directions, the corresponding mirror image of that molecule will have the same relative stereochemistry. On the other hand, if the "absolute stereochemistry" is indicated by drawing substituents or groups of a molecule in certain directions, a particular enantiomer of that molecule is intended.

Compounds

An aspect disclosed herein relates to a compound according to formula (I)

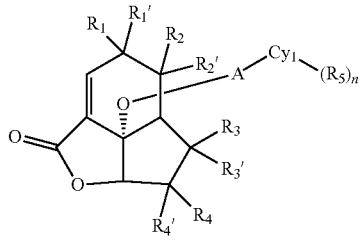

(I)

wherein $R_1$ and $R_1'$ are independently selected from the group consisting of H, C1-5 alkyl, C1-5 fluoroalkyl, halo, cyano, nitro, —OH, OC1-5 alkyl, C1-5 alkyleneOH, C1-5 alkyleneOC1-5 alkyl, C3-8 non-aromatic carbocycle, OC1-5 fluoroalkyl, C1-3 alkyleneOC1-5 fluoroalkyl, OC(O)C1-5 alkyl, C1-3 alkyleneOC(O)C1-5 alkyl, OC2-3 alkyleneNH$_2$, OC2-3 alkyleneNH(C1-5 alkyl), OC2-3 alkyleneN(C1-5 alkyl)$_2$ in which the C1-5 alkyl may be the same or different, —NH$_2$, —NH(C1-5 alkyl), C1-3 alkyleneNH$_2$, C1-3 alkyleneNH(C1-5 alkyl), —N(C1-5 alkyl)$_2$ in which the C1-5 alkyl may be the same or different, C1-3 alkyleneN(C1-5 alkyl)$_2$ in which the C1-5 alkyl may be the same or different, NHC(O)C1-5 alkyl, N(C1-5 alkyl)C(O)C1-5 alkyl, C1-3 alkyleneNHC(O)C1-5 alkyl, C1-3 alkyleneN(C1-5 alkyl)C(O)C1-5 alkyl, NHaryl, C1-3 alkyleneNHaryl, wherein the aryl is unsubstituted or substituted with one or more substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, NH2, NH(C1-5 alkyl), and N(C1-5 alkyl)$_2$ in which the C1-5 alkyl may be the same or different, NHheteroaryl, C1-3 alkyleneNHheteroaryl, wherein said heteroaryl is a 5- or 6-membered heteroaryl, said heteroaryl being unsubstituted or substituted with a one or several independently selected from C1-5 alkyl, C(O)NH$_2$, C(O)NHC1-5 alkyl, C1-3 alkyleneC(O)NH$_2$, C1-3 alkyleneC(O)NHC1-5 alkyl, C(O)N(C1-5 alkyl)$_2$ in which the C1-5 alkyl may be the same or different, C1-3 alkyleneC(O)N(C1-5 alkyl)$_2$ in which the C1-5 alkyl may be the same or different, C(O)N(C4-5 alkylene), C1-3 alkyleneC(O)N(C4-5 alkylene), C(O)OH, C(O)OC1-5 alkyl, C1-3 alkyleneC(O)OH, C1-3 alkyleneC(O)OC1-5 alkyl, and a 3- to 8-membered non-aromatic heterocycle, aryl, C1-3 alkylene-aryl, wherein the aryl is unsubstituted or substituted with one or several substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, —NH$_2$, —NH(C1-5 alkyl), and N(C1-5 alkyl)$_2$ in which the C1-5 alkyl may be the same or different, heteroaryl, C1-3 alkylene-heteroaryl, wherein said heteroaryl is a 5- or 6-membered heteroaryl, said heteroaryl being unsubstituted or substituted with one or several independently selected C1-5 alkyl groups, halo, cyano, —CH$_2$-cyano, —SH, SC1-5 alkyl, SO$_2$H, SO$_2$C1-5 alkyl, C1-3 alkyleneSO$_2$H, C1-3 alkyleneSO$_2$C1-5 alkyl, nitro, C(O)H, C(O)C1-5 alkyl, C(O)C1-5 fluoroalkyl, NHSO$_2$C1-5 alkyl, N(C1-C3 alkyl)SO$_2$C1-C5 alkyl, NHSO$_2$C1-5 fluoroalkyl, and N(C1-C5 alkyl)SO$_2$C1-5 fluoroalkyl, —SH, —SC1-5 alkyl, C1-5 alkylene-SH, C1-5 alkylene-SC1-5 alkyl, SC1-5 fluoroalkyl, C1-5 alkyleneSC1-5 fluoroalkyl, SO2C1-5 alkyl, C1-5 alkylene-SO2C1-5 alkyl, SO2C1-5 fluoroalkyl, C1-5 alkylene-SO2C1-5 fluoroalkyl, SO$_2$NH$_2$, SO$_2$NH(C1-5 alkyl), SO$_2$N(C1-5 alkyl)$_2$ in which the C1-5 alkyl may be the same or different, C1-5 alkyleneSO$_2$NH$_2$, C1-5 alkyleneSO$_2$NH(C1-5 alkyl), C1-5 alkyleneSO$_2$N(C1-5 alkyl)$_2$ in which the C1-5 alkyl may be the same or different, SO2NHaryl, C1-5 alkyleneSO2NHaryl, wherein the aryl is unsubstituted or substituted with a one or several substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, —NH$_2$, —NH(C1-5 alkyl), and N(C1-5 alkyl)$_2$ in which the C1-5 alkyl may be the same or different, SO2N(C1-5 alkyl)aryl, and C1-5 alkyleneSO2N(C1-5 alkyl)aryl, wherein the aryl is unsubstituted or substituted with a one or several substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, —NH$_2$, —NH(C1-5 alkyl), and N(C1-5 alkyl)$_2$ in which the C1-5 alkyl may be the same or different;

$R_2$, $R_2'$, $R_3$, and $R_3'$ are each independently selected from the group consisting of H, halo, —OH, C1-5 alkyl, and C1-5 fluoroalkyl;

$R_4$ and $R_4'$ are independently selected from the group consisting of H, C1-5 alkyl, aryl, and CH$_2$aryl;

A is selected from the group consisting of a bond, C1-C5 alkylene or NR$_{10}$;

$R_{10}$ is H or C1-C3 alkyl;

$Cy_1$ is a ring selected from the group consisting of aryl, heteroaryl, a non-aromatic carbocycle, and a non-aromatic heterocycle;

$R_5$ is independently selected from the group consisting of C1-8 alkyl, C1-5 haloalkyl, halo, cyano, —CH$_2$-cyano, —OH, OC1-5 alkyl, C1-8 alkyleneOC1-5 alkyl, O-aryl, C1-8 alkylene-O-aryl, —SH, SC1-5 alkyl, SO$_2$H, SO$_2$C1-5 alkyl, C1-3 alkyleneSO$_2$H, C1-3 alkyleneSO$_2$C1-5 alkyl, OC1-3 fluroroalkyl, C1-3 alkyleneOC1-3 fluroroalkyl, NH2, NH(C1-3 alkyl), C1-3 alkylene-NH2, C1-3 alkyleneNH(C1-3 alkyl), N(C1-5 alkyl)$_2$ in which the C1-5 alkyl may be the same or different, C1-3 alkyleneN(C1-5 alkyl)$_2$ in which the C1-5 alkyl may be the same or different, C(O)OH, C(O)OC1-5 alkyl, C1-3 alkyleneC(O)OH, C1-3 alkyleneC(O)OC1-5 alkyl, OC(O)H, OC(O)C1-5 alkyl, C1-3 alkyleneOC(O)H, C1-3 alkyleneOC(O)C1-5 alkyl, NHC(O)H, NHC(O)C1-5 alkyl, N(C1-3 alkyl)C(O)H, N(C1-3 alkyl)C(O)C1-5 alkyl, C1-3 alkyleneNHC(O)H, C1-3 alkyleneNHC(O)C1-5 alkyl, C1-3 alkyleneN(C1-3 alkyl)C(O)H, C1-3 alkyleneN(C1-3 alkyl)C(O)C1-5 alkyl, C(O)NH2, C(O)NH(C1-3 alkyl), C1-3 alkyleneC(O)NH2, C1-3 alkyleneC(O)NH(C1-3 alkyl), C(O)N(C1-5 alkyl)$_2$, in which the C1-5 alkyl may be the same or different, C1-3 alkyleneC(O)N(C1-5 alkyl)$_2$, in which the C1-5 alkyl may be the same or different, nitro, C(O)H, C(O)C1-C5 alkyl, NHSO2C1-C3 alkyl, N(C1-C3 alkyl)SO2C1-C3 alkyl, NHSO2C1-C3 fluoroalkyl, N(C1-C3 alkyl)SO2C1-C3 fluoroalkyl, OC2-C3alkyleneNH2, OC2-C3alkyleneNH(C1-C3 alkyl), OC2-C3alkyleneN(C1-C3 alkyl)$_2$ in which the C1-3 alkyl may be the same or different, and

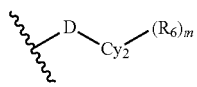

wherein

D is selected from the group consisting of a bond, C1-3 alkylene, O—C1-3 alkylene, C1-3 alkylene-O—C1-3 alkylene, OC(O)C1-3 alkylene, C1-3 alkylene-OC(O)—C1-3 alkylene, C(O)OC1-3 alkylene, C1-3 alkylene-C(O)O—C1-3 alkylene, C(O)N(H)(C1-3 alkylene), C(O)N(C1-3 alkyl)(C1-3 alkylene), C1-3 alkylene-C(O)N(H)(C1-3 alkylene), C1-3 alkylene-C(O)N(C1-3 alkyl)(C1-3 alkylene), N(H)C(O)C1-3 alkylene, N(C1-3 alkyl)C(O)C1-3 alkylene, C1-3 alkylene-N(H)C(O)C1-3 alkylene, C1-3 alkylene-N(C1-3 alkyl)C(O)C1-3 alkylene, —NHSO2-, —SO2NH—, SO2, SO, C(O), C1-3 alkylene-C(O), C(O)C1-3 alkylene, C1-3 alkylene C(O)C1-3 alkylene, NH, N(C1-3 alkyl), NH—C1-3 alkylene, N(C1-3 alkyl)-C1-3 alkylene, C1-3 alkylene-NH, C1-3 alkylene-N(C1-3 alkyl), C1-3 alkylene-NH—C1-3 alkylene, C1-3 alkylene-N(C1-3 alkyl)-C1-3 alkylene, and S;

Cy2 is a 5-membered heteroaryl, a 6-membered heteroaryl, phenyl, a 3- to 8-membered non-aromatic heterocycle or a C3-8 non-aromatic carbocycle;

m is an integer selected from the group consisting of 0, 1, 2, 3, 4, and 5;

$R_6$ is independently selected from oxo, C1-5 alkyl, C1-5 fluoroalkyl, halo, cyano, —CH$_2$-cyano, —OH, OC1-5 alkyl, C1-5 alkylene-OH, C1-5 alkyleneOC1-5 alkyl, —SH, SC1-5 alkyl, SO2H, SO2C1-5 alkyl, C1-3 alkyleneSO2H, C1-3 alkyleneSO2C1-5 alkyl, OC1-3 fluoroalkyl, C1-3 alkyleneOC1-3 fluoroalkyl, NH2, NH(C1-3 alkyl), C1-3 alkylene-NH2, C1-3 alkylene-NH(C1-3 alkyl), N(C1-5 alkyl)2 in which the C1-5 alkyl may be the same or different, C1-3 alkyleneN(C1-5 alkyl)2 in which the C1-5 alkyl may be the same or different, C(O)OH, C(O)OC1-5 alkyl, C1-3 alkylene-C(O)OH, C1-3 alkylene-C(O)OC1-5 alkyl, OC(O)H, OC(O)C1-5 alkyl, C1-3 alkylene-OC(O)H, C1-3 alkylene-OC(O)C1-5 alkyl, NHC(O)H, NHC(O)C1-3 alkyl, N(C1-3 alkyl)C(O)H, N(C1-3 alkyl)C(O)C1-3 alkyl, C1-3 alkylene-NHC(O)H, C1-3 alkylene-NHC(O)C1-3 alkyl, C1-3 alkylene-N(C1-3 alkyl)C(O)H, C1-3 alkylene-N(C1-3 alkyl)C(O)C1-3 alkyl, C(O)NH2, C(O)NH(C1-3 alkyl), C1-3 alkylene-C(O)NH2, C1-3 alkylene-C(O)NH(C1-3 alkyl), C(O)N(C1-5 alkyl)2 in which the C1-5 alkyl may be the same or different, C1-3 alkyleneC(O)N(C1-5 alkyl)2 in which the C1-5 alkyl may be the same or different, C(O)N(C4-5 alkylene), C1-3 alkyleneC(O)N(C4-5 alkylene), nitro, C(O)H, C(O)C1-C5 alkyl, C(O)C1-C3 fluoroalkyl, NHSO$_2$C1-C3 alkyl, N(C1-C3 alkyl)SO$_2$C1-C3 alkyl, NHSO$_2$C1-C3 fluoroalkyl, N(C1-C3 alkyl)SO$_2$C1-C3 fluoroalkyl, OC2-C3 alkyleneNH$_2$, OC2-C3 alkyleneNH(C1-C3 alkyl), and OC2-C3 alkyleneN(C1-C3 alkyl)2 in which the C1-3 alkyl may be the same or different; or when two R6 are present, each R6 is combined to form a fused ring or spiro ring with Cy2;

n is an integer selected from the group consisting of 0, 1, and 2;

as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

Another aspect disclosed herein relates to a compound according to formula (II)

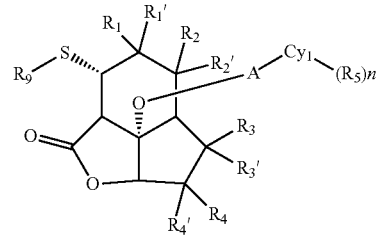

wherein $R_1$, $R_{1'}$, $R_2$, $R_{2'}$, $R_3$, $R_{3'}$, $R_4$, $R_{4'}$, A, $Cy_1$, $R_5$, and n are defined as above in respect of compounds of formula (I);

$R_9$ is a moiety according to formula (III),

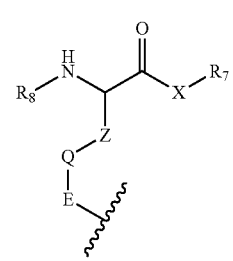

wherein the waved line indicates the point of attachment to the sulfur atom in formula (II);

Z is a C1-5 alkylene;

Q is a bond, a phenylene, or a heteroarylene, wherein said heteroarylene is a 5- or 6-membered heteroarylene;

E is a bond or a C1-5 alkylene;

X is selected from the group consisting of NH, NC1-C5 alkyl or "O" (oxygen);

R7 is selected from the group consisting of H, C1-C10 alkyl, C1-5 alkyleneN(C1-5 alkyl)$_2$ in which the C1-5 alkyl may be the same or different, aryl, C1-3 alkylene-aryl wherein the aryl is unsubstituted or substituted with a one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, nitro, cyano, NH$_2$, NH(C1-5 alkyl), and N(C1-5 alkyl)$_2$ in which the C1-5 alkyl may be the same or different, C1-3 alkylene heteroaryl, wherein said heteroaryl is a 5- or 6-membered heteroaryl, said heteroaryl being unsubstituted or substituted with a one or several independently selected C1-5 alkyl groups, an amino acid residue selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (III) at the N-terminal of the amino acid residue and optionally esterfied at the C-terminal with a C1-5 monohydric alkanol, and a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (III) at the N-terminal of the peptide and optionally esterfied at the C-terminal with a C1-5 monohydric alkanol;

provided that R7 cannot be H if X is "O" (oxygen); and R8 is selected from the group consisting of:

C(O)C1-C6 alkyl, C(O)OC1-C6 alkyl,

C(O)-aryl, C(O)C1-3 alkylene-aryl wherein the aryl is unsubstituted or substituted with a one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, nitro, cyano, $NH_2$, NH(C1-5 alkyl), and N(C1-5 alkyl)$_2$ in which the C1-5 alkyl may be the same or different, C(O)-heteroaryl, C(O)C1-3 alkylene-heteroaryl wherein said heteroaryl is a 5- or 6-membered heteroaryl, said heteroaryl being unsubstituted or substituted with one or several independently selected C1-5 alkyl groups, an amino acid residue selected from the group consisting of alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, which amino acid residue is connected to the moiety according to formula (III) at the C-terminal of the amino acid residue, and which amino acid residue is optionally N-acylated, wherein said acyl group is selected from the group consisting C(O)C1-C6 alkyl, C(O)-aryl, and C(O)C1-3 alkylene-aryl, wherein the aryl is unsubstituted or substituted with a one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, nitro, cyano, $NH_2$, NH(C1-5 alkyl), and N(C1-5 alkyl)$_2$ in which the C1-5 alkyl may be the same or different, and a di-, a tri-, or a tetrapeptide residue, wherein the amino acid residues in said peptide residue are independently selected from the group consisting alanine, arginine, asparagine, aspartic acid, cysteine, glutamine, glutamic acid, glycine, histidine, isoleucine, leucine, lysine; methionine, phenylalanine, proline, threonine, tryptophan, tyrosine and valine, the peptide residue being connected to the moiety according to formula (III) at the C-terminal of the peptide, and the N-terminal of the peptide optionally being N-acelyated, wherein said acyl group is selected from the group consisting C(O)C1-C6 alkyl, C(O)-aryl, and C(O)C1-3 alkylene-aryl, wherein the aryl is unsubstituted or substituted with a one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, nitro, cyano, $NH_2$, NH(C1-5 alkyl), and N(C1-5 alkyl)$_2$ in which the C1-5 alkyl may be the same or different;

as a free base, an acid in its non-charged protonated form, a pharmaceutically acceptable addition salt, solvate, solvate of a salt thereof, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

As with any group of structurally related compounds which possess a particular utility, certain embodiments of variables of the compounds of formulae (I) and (II) may be particularly useful in their end use application.

According to an embodiment, the compounds of formula (I) have the relative or absolute stereochemistry according to formula (Ia):

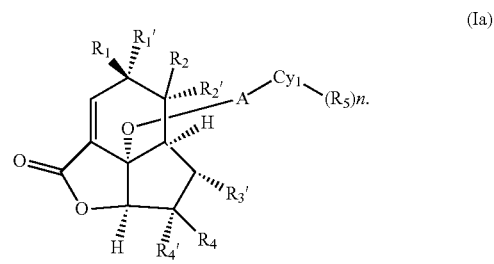

The individual diastereomers or enantiomers in a diastereomeric or scalemic mixture, respectively, may be present in the same amount, thus constituting a racemic mixture in the latter case, or in different amounts. However, it is preferred if one of the diastereomers or enantiomers prevails. Accordingly, its is preferred if one of the diastereomers or enantiomers is more than 50%, such as more than 75%, 90%, 95% or even more than 99%.

In some embodiments A is selected from the group consisting of —$CH_2$—, —$CH_2CH_2$—, and —$CH_2CH_2CH_2$—. According to a particular embodiment A is —$CH_2$—.

Some embodiments relate to $Cy_1$ being selected from the group consisting of phenyl, 5-membered heteroaryl, 6-membered heteroaryl, 5-membered saturated carbocycle, 6-membered saturated carbocycle, 5-membered saturated heterocycle, and a 6-membered saturated heterocycle.

In some embodiments $Cy_1$ is selected from the group consisting of phenyl, pyridinyl, pyridazinyl, pyrimidinyl, pyrazinyl, pyrrolyl, imidazolyl, pyrazolyl, oxazolyl, isoxazolyl, isothiazolyl and thiazolyl.

In some embodiments $Cy_1$ is selected from the group consisting of pyridinyl, pyridazinyl, pyrimidinyl, pyrazinyl, pyrrolyl, imidazolyl, pyrazolyl, oxazolyl, isoxazolyl, isothiazolyl and thiazolyl. In a further embodiment $Cy_1$ is pyridinyl.

In some embodiments $Cy_1$ is a bicyclic aryl or a bicyclic heteroaryl. In some embodiments $Cy_1$ is selected from the group consisting of naphthyl, tetralinyl, quinolyl, tetrahydroquinolyl, isoquinolyl, tetrahydroisoquinolyl, quinazolinyl, quinoxalinyl, tetrahydroquinoxalinyl, indolyl, isoindolyl, indolinyl, isoindolinyl, indazolyl, benzimidazolyl, benzofuranyl, dihydrobenzofuranyl, benzothienyl, benzthiazolyl, and benzothienyl.

In some embodiments $Cy_1$ is selected from the group consisting of C6-10 aryl, C3-9 heteroaryl, a C3-8 non-aromatic carbocycle, and a C3-7 non-aromatic heterocycle. In some embodiments $Cy_1$ is selected from the group consisting of C3-5 heteroaryl, a C4-6 non-aromatic carbocycle, and a C3-5 non-aromatic heterocycle.

In some embodiments $R_5$ is selected from the group consisting of C1-C4 alkyl, C1-C4 haloalkyl, —OH, C1-C4 alkoxy, C1-C4 alkylamino, (C1-C4 alkyl)$_2$-amino, aryl, aryl fused with $Cy_1$, aryloxy, heteroaryloxy, C1-C4 alkyl-C(O)—, C1-C4 alkyl-C(O)O—, C1-C4 alkyl-O(O)C—, C1-C4 alkyl-C(O)NH—, C1-C4 alkyl-NH(O)C—, C1-C4 alkyl-C(O)N(C1-C3 alkyl)-, C1-C4 alkyl-N(C1-C3 alkyl)(O)C—, halogen, nitro, cyano, a 5-membered saturated heterocycle, a 6-membered saturated heterocycle, a 5-membered saturated heterocycle fused with $Cy_1$, and a 6-membered saturated heterocycle fused with $Cy_1$.

In some embodiments $R_5$ is selected from the group consisting of methyl, methoxy, —$NH_2$, fluorine, $CF_3$, —NH(CO)C(CH$_3$)$_3$, phenoxy, acetyl, $CH_3$—C(O)O—, $CH_3$—O(O)C—, pyrrolidinyl, morpholinyl, phenyl fused with $Cy_1$, and N-methyl morpholinyl fused with $Cy_1$.

In some embodiments the integer n is 0 or 1.

According to an embodiment $R_1$ and $R_1'$ are independently selected from the group consisting of hydrogen, C1-C5 alkyl, preferably methyl, C1-5 fluoroalkyl, —OH, C1-C5 alkoxy, preferably methoxy, and halogen, preferably fluorine.

According to some embodiments $R_1$ and $R_1'$ are independently selected from the group consisting of hydrogen, methyl, fluorine, and methoxy.

In one embodiment $R_1$ is methyl and $R_1'$ is hydrogen. In another embodiment $R_1$ is fluorine or methoxy and $R_1'$ is methyl.

Some embodiments relate to $R_2$, $R_2'$, $R_3$, and $R_3'$ being all hydrogen.

Another embodiment relates to $R_4$ and $R_4'$ being both hydrogen.

According to another embodiment $R_9$ is a moiety according to formula (V),

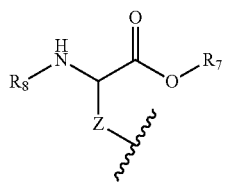

(V)

wherein the waved line indicates the point of attachment to the sulfur atom in formula (II);

Z is a C1-3 alkylene;

R7 is selected from the group consisting of C1-C10 alkyl, C1-5 alkyleneN(C1-5 alkyl)$_2$ in which the C1-5 alkyl may be the same or different, aryl, C1-3 alkylene aryl, wherein the aryl is unsubstituted or substituted with a one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, cyano, NH$_2$, NH(C1-5 alkyl), and N(C1-5 alkyl)$_2$ in which the C1-5 alkyl may be the same or different, C1-3 alkylene heteroaryl, wherein said heteroaryl is a 5- or 6-membered heteroaryl, said heteroaryl being unsubstituted or substituted with a one or several independently selected C1-5 alkyl groups; and and R8 is selected from the group consisting of C(O)C1-C6 alkyl, C(O)OC1-C6 alkyl, C(O)aryl, C(O)C1-3 alkylene aryl, wherein the aryl is unsubstituted or substituted with one or several substituents independently selected from the group consisting of C1-5 alkyl, C1-5 fluoroalkyl, halo, —OH, —OC1-5 alkyl, C1-5 alkyleneOH, C1-5 alkyleneOC1-5 alkyl, cyano, NH$_2$, NH(C1-5 alkyl), and N(C1-5 alkyl)$_2$ in which the C1-5 alkyl may be the same or different, C(O)heteroaryl, C(O)C1-3 alkylene heteroaryl, wherein said heteroaryl is a 5- or 6-membered heteroaryl, said heteroaryl being unsubstituted or substituted with a one or several independently selected C1-5 alkyl groups.

In another embodiment the compound of formula (I) or formula (II) is selected from the group consisting of:

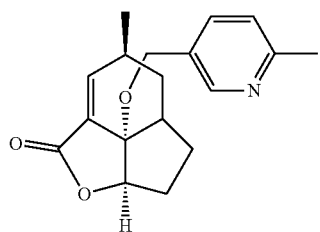

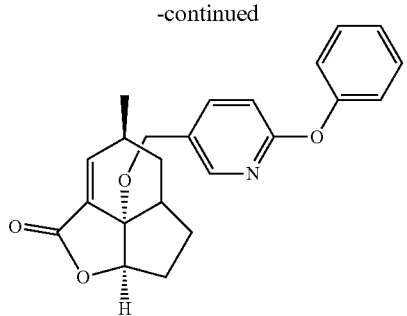

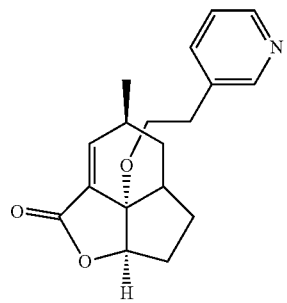

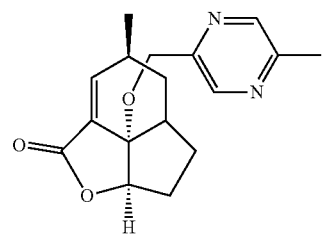

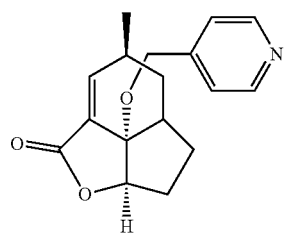

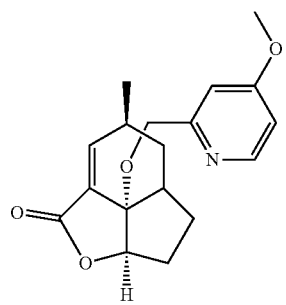

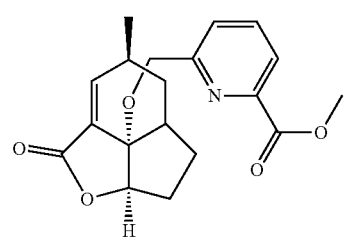

-continued
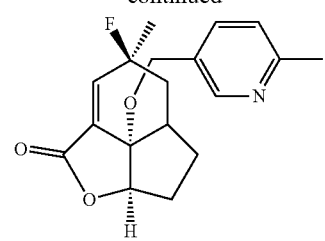
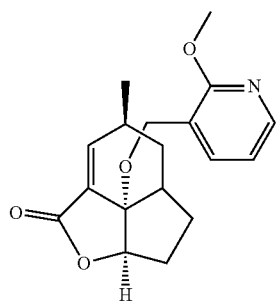
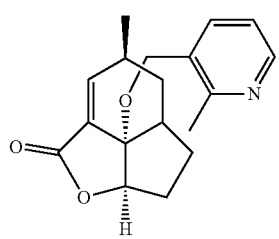
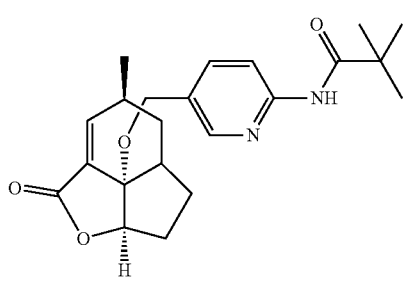
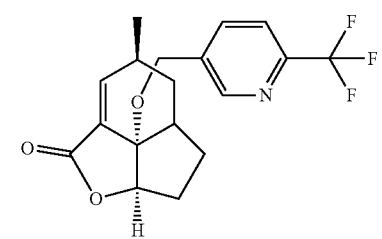
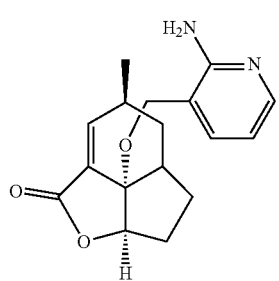
-continued
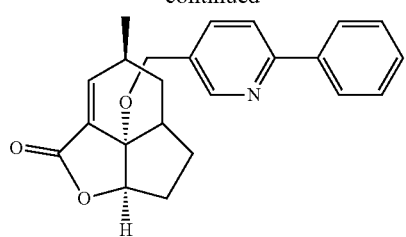
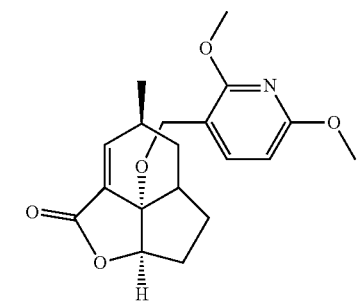
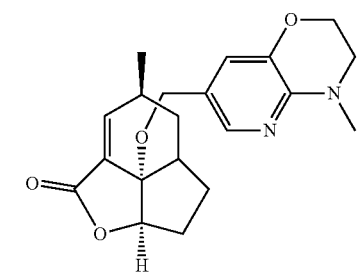
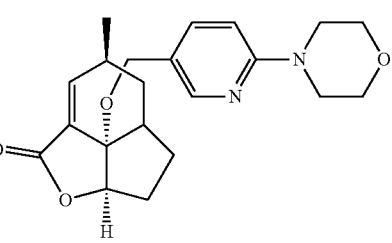
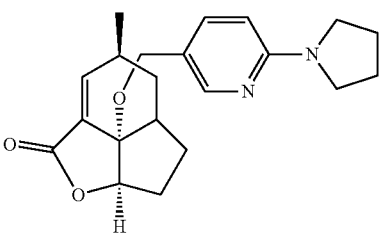
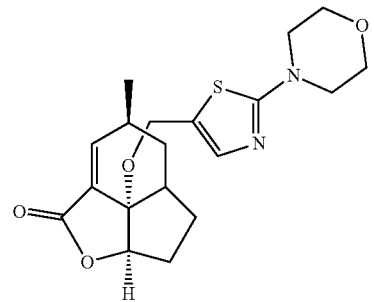

-continued
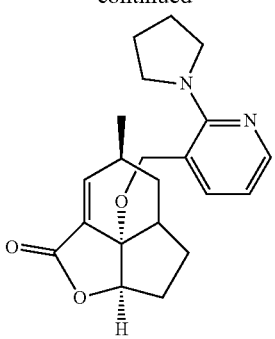
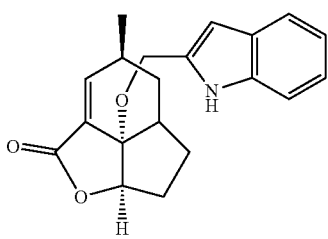
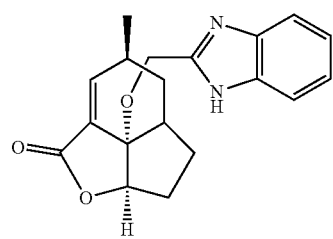
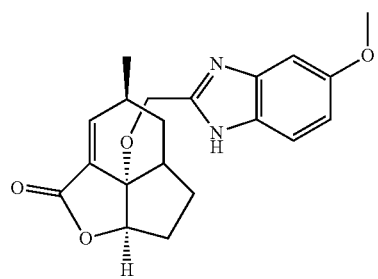
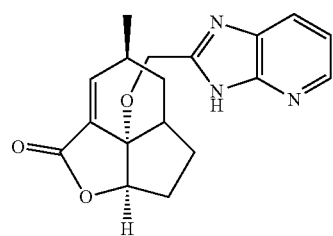
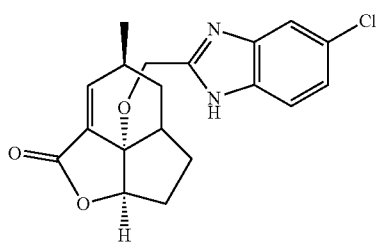
-continued
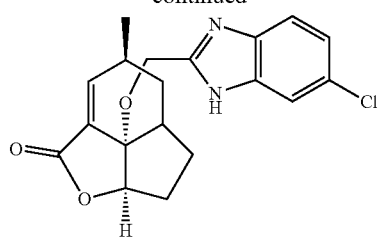
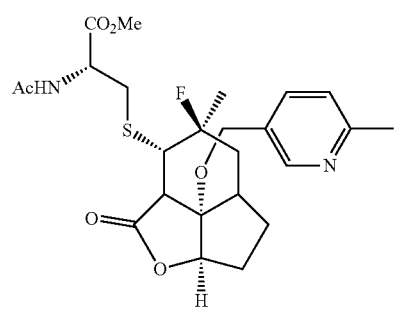
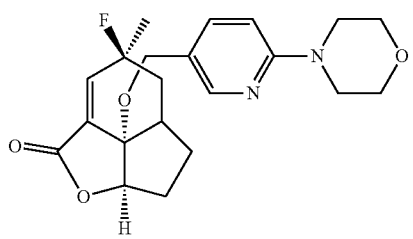
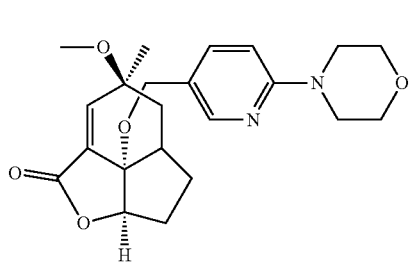
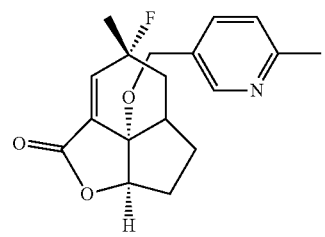
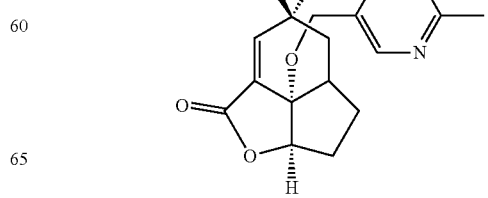

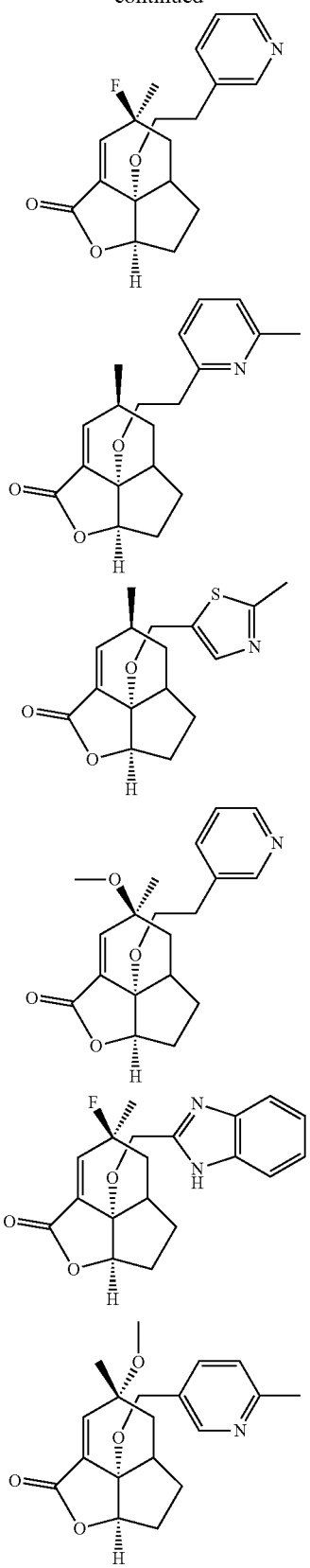

wherein the indicated stereochemistry is relative or absolute stereochemistry.

The present inventors have surprisingly found that in some embodiments the compounds of formula (I) in which Cy1 is a heteroaryl or non-aromatic heterocycle containing a nucleophilic nitrogen atom, react intramolecularly through a conjugate or Michael addition reaction to form a compound of formula (X)

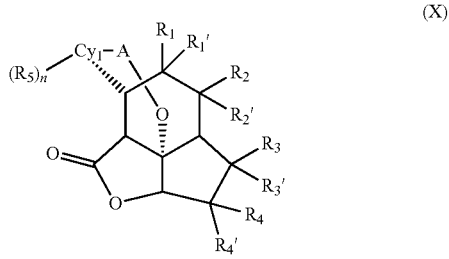

(X)

wherein $R_1$, $R_{1'}$, $R_2$, $R_{2'}$, $R_3$, $R_{3'}$, $R_4$, $R_{4'}$, A, $Cy_1$, $R_5$, and n are defined as above in respect of compounds of formula (I).

Some embodiments of compounds of formula (X) relate to compounds of formula (XI)

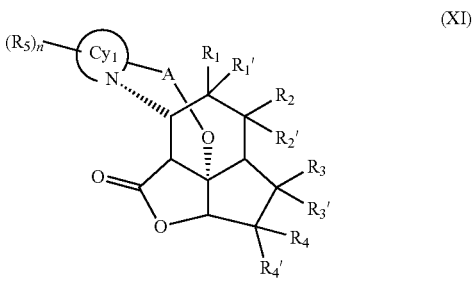

(XI)

wherein $R_1$, $R_{1'}$, $R_2$, $R_{2'}$, $R_3$, $R_{3'}$, $R_4$, $R_{4'}$, A, $Cy_1$, $R_5$, and n are defined as above in respect of compounds of formula (I).

Some embodiments of compounds of formula (X) relate to compounds of formula (XII)

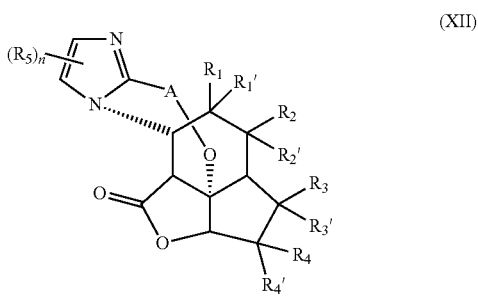

(XII)

wherein $R_1$, $R_{1'}$, $R_2$, $R_{2'}$, $R_3$, $R_{3'}$, $R_4$, $R_{4'}$, A, $R_5$, and n are defined as above in respect of compounds of formula (I).

In some embodiments of the compounds of formula (X), Cy1 is benzimidazolyl which provides compounds of formula (XIII):

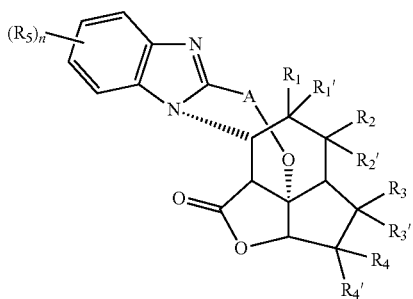

wherein $R_1$, $R_{1'}$, $R_2$, $R_{2'}$, $R_3$, $R_{3'}$, $R_4$, $R_{4'}$, A, $R_5$, and n are defined as above in respect of compounds of formula (I).

In one embodiment the compound of formula (XIII) is

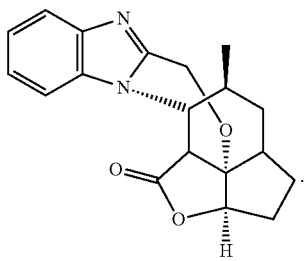

Without wishing to be bound by theory, it is believed that under physiological conditions the tetracyclic compounds of formulae (X), (XI), (XII), and (XIII) undergo an intramolecular elimination reaction to form the compounds of formula (I) according to the following example:

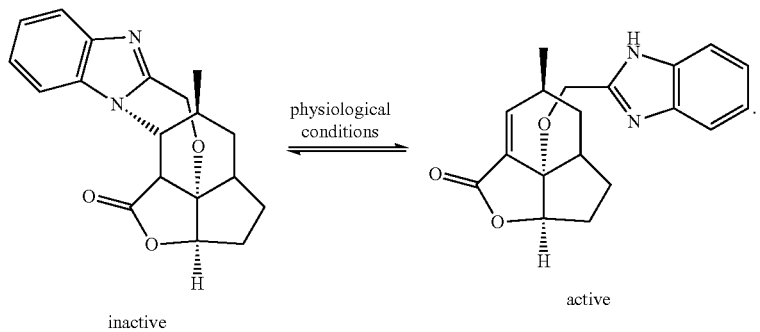

Thus, also compounds according to formula (X) are anti-proliferative under physiological conditions.

Pharmaceutical Compositions

Compounds disclosed herein, e.g. compounds according to formulae (I), (II) (X), (XI), (XII), and (XIII) or preferred selections thereof, may be formulated into conventional pharmaceutical compositions, e.g. medicaments. According to an embodiment, there is thus provided a pharmaceutical composition comprising a compound as disclosed herein and at least one pharmaceutically acceptable carrier or excipient. In this context "pharmaceutically acceptable" is intended to mean an excipient or carrier that, at the dosage and concentrations employed, does not cause any unwanted effects in the patients to whom it is administered. Such pharmaceutically acceptable carriers and excipients are well-known in the art. Further, pharmaceutical composition, as described herein, may also comprise pharmaceutically diluents, stabilizers and the like.

The pharmaceutically acceptable carriers may be either solid or liquid.

Pharmaceutical compositions may typically be provided either as solid or as liquid preparations.

Solid form preparations include, but are not limited to, powders, tablets, dispersible granules, capsules, cachets, and suppositories. Powders, tablets, dispersible granules, capsules, cachets may be used as solid dosage forms suitable for oral administration, while suppositories may be used for rectal administration.

A solid carrier may be one or more substances, which may also act as diluent, flavoring agent, solubilizer, lubricant, suspending agent, binder, or tablet disintegrating agent. A solid carrier may also be an encapsulating material. Suitable carriers include, but are not limited to, magnesium carbonate, magnesium stearate, talc, lactose, sugar, pectin, dextrin, starch, tragacanth, methyl cellulose, sodium carboxymethyl cellulose, low-melting wax, cocoa butter, and the like.

In powders, the carrier is normally a finely divided solid, which is in a mixture with the compound as disclosed herein, also typically being finely divided. In tablets, the active component may be mixed with the carrier having the necessary binding properties in suitable proportions and compacted in the shape and size desired.

For preparing suppository compositions, a low-melting wax, such as a mixture of fatty acid glycerides and cocoa butter, may first be melted and the active ingredient, like a compound of the invention, may then be dispersed therein by, for example, stirring. The molten homogeneous mixture may then be poured into convenient sized moulds and allowed to cool and solidify.

The term composition is also intended to include the formulation of the active component with encapsulating material as a carrier providing a capsule in which the active component (with or without other carriers) is surrounded by a carrier which is thus in association with it. Similarly, cachets are included.

Liquid form preparations include, but are not limited to, solutions, suspensions, and emulsions. For example, dissolvation or dispersion of the compounds disclosed herein in sterile water or mixture of water and propylene glycol may provide liquid preparations suitable for parenteral administration. Liquid compositions may also be formulated in solution in aqueous polyethylene glycol solution.

Aqueous solutions for oral administration may be prepared by dissolving the active component, like a compound of the invention, in water and adding suitable colorants, flavoring agents, stabilizers, and thickening agents as desired. Aqueous suspensions for oral use may be made by dispersing the finely divided active component in water together with a viscous material such as natural synthetic gums, resins, methyl cellulose, sodium carboxymethyl cellulose, and other suspending agents known to the pharmaceutical formulation art. Exemplary compositions intended for oral use may contain one or more coloring, sweetening, flavoring and/or preservative agents.

A pharmaceutical composition according to embodiments disclosed herein may be administered through different routes such as, but not limited to, intravenously, intraperitonealy, intramuscularly, intranasaly, subcutaneously, sublingually, rectally, orally as well as through inhalation or insufflation.

Depending on the mode of administration, the pharmaceutical composition may include from about 0.05 wt % (percent by weight) to about 99 wt %, such as about 0.10 wt % to about 50 wt %, about 0.5 wt % to about 30, or about 1.0 wt % to about 25 wt %, of a compound disclosed herein, all percentages by weight being based on the total weight of the composition.

Therapy

Compounds disclosed herein, e.g. compounds according to formulae (I), (II) (X), (XI), (XII), and (XIII) or preferred selections thereof, as well as pharmaceutical compositions comprising such a compound, may be used in therapy.

Compounds disclosed herein, e.g. compounds according to formulae (I), (II) (X), (XI), (XII), and (XIII) or preferred selections thereof, as well as pharmaceutical compositions comprising such a compounds, may be used for the treatment of various diseases or conditions in humans or mammals, such as dogs, cats, horses, cows or other mammals; in particular domestic mammals. Mammals may be treated for the same diseases and conditions as humans may be treated for.

When used in therapy, a pharmaceutical composition according to embodiments herein may be administered to the patient in a pharmaceutically effective dose. By "pharmaceutically effective dose" is meant a dose that is sufficient to produce the desired effects in relation to the condition for which it is administered. The exact dose may be dependent on the activity of the compound, manner of administration, nature and severity of the disorder and/or disease and the general conditions, such as age and body weight of the patient.

A therapeutically effective amount for the practice of the present invention may be determined by one of ordinary skill in the art using known criteria including the age, weight and response of the individual patient, and interpreted within the context of the disease which is being treated or which is being prevented.

Treatment of STAT3 Signaling Related Disorder and Inhibition of Cancer Cell Proliferation The parent compound galiellalactone and related compounds (cf. WO 2012/010555) are covalent inhibitors of STAT3, binding directly to STAT3 and preventing DNA binding. As described herein above, the transcription factor STAT3 has emerged as a highly promising target for the treatment of various cancers, e.g. castration resistant prostate cancer (CRPC). In CRPC, constitutive activation of STAT3 is implicated in drug resistance, the progression of androgen independent growth, metastasis, immune avoidance and tumor growth.

Galiellalactone has indeed been found to inhibit proliferation of DU145 prostate cancer cells (cf. Hellsten et al; Prostate 68; 269-280, 2008). Without being bound to any theory, it is believed that Galiellalactone induces apoptosis by down regulating STAT3 related genes.

As the compounds disclosed herein are significantly more selective for STAT3 than galiellalactone (cf. experimental) they may be used in the treatment or prevention of a STAT3 signaling related disorder. Especially, compounds disclosed herein may be used in the treatment of cancer, as they inhibit proliferation of cancer cells.

An embodiment thus relates to compounds and pharmaceutical compositions disclosed herein, e.g. compounds according to formulae (I), (II) (X), (XI), (XII), and (XIII) or preferred selections thereof, for use in treatment or prevention of a STAT3 signaling related disorder. Examples of STAT3 signaling related disorders include various cancers, such as solid cancers and hematological cancer, benign tumors, hyperproliferative diseases, inflammation, autoimmune diseases, graft or transplant rejections, delayed physiological function of grafts or transplants, neurodegenerative diseases or viral infections, such as from solid cancers and hematological cancers.

In addition to the effect on STAT3, galiellalactone has also been shown to block TGF-beta signaling (Rudolph et al Cytokine. 2013 January; 61(1):285-96) and to be effective in an in vivo murine model of allergic asthma (Hausding et al Int Immunol. 2011 January; 23(1):1-15).

Regardless of their interference with STAT3 signaling or not, compounds and pharmaceutical compositions disclosed herein may be used in the treatment or prevention of cancer. Another embodiment thus relates to compounds and pharmaceutical compositions disclosed herein for use in the prevention or treatment of cancer, such as solid cancers or hematological cancers.

Examples of solid cancers include, but are not limited to, sarcomas, breast cancer, prostate cancer, head and neck cancer, brain tumors, colorectal cancer, lung cancer, pancreatic cancer, cervical cancer, ovarian cancer, melanoma, gastric cancers, renal cell carcinoma, endometrial cancer, sarcomas and hepatocellular carcinomas. Examples hematological cancers include, but are not limited to, chronic myelogenous leukemia, acute myelogenous leukemia, cutaneous T-cell lymphoma, Hodgkin's disease, anaplastic large-cell lymphoma and Burkitt's lymphoma.

Further, the cancers to be treated by compounds and pharmaceutical compositions disclosed herein, are according to an embodiment selected from the group consisting of leukemia, lymphomas, multiple myeloma, breast cancer, prostate carcinoma, lung cancer (non-small-cell), renal cell carcinoma lung cancer, hepatocellular carcinoma, cholangiocarcinoma, ovarian carcinoma, pancreatic adenocarcinoma, melanoma, glioblastoma and head and neck squamous cell carcinoma.

Regardless of their interference with STAT3 signaling or not, compounds and pharmaceutical compositions disclosed herein may be used in the treatment or prevention of benign tumors. Another embodiment thus relates to compounds and pharmaceutical compositions disclosed herein for use in the prevention or treatment of benign tumors, including for example Cardiac myxoma and Castleman's disease.

Compounds and pharmaceutical compositions disclosed herein may inhibit proliferation or angiogenesis, induces apoptosis, sensitizes to apoptosis or causes cytotoxicity of cancer cells, including cancer stem cells e.g. leukemic, prostate and breast cancer stem cells. Preferably, the cancer displays elevated or aberrant STAT3 signaling or activity, constitutively phosphorylated or active STAT3 or increased STAT3 protein expression. According to an embodiment, compounds and pharmaceutical compositions disclosed herein are thus used to inhibit the growth or migration of cells. These cells may have elevated or aberrant STAT3 signaling or activity, constitutively phosporylated or active STAT3 or increased STAT3 protein expression. Hence, associated diseases and disorders, such as hyperproliferative diseases, may be treated or prevented by use of compounds and pharmaceutical compositions disclosed herein. Another embodiment thus relates to compounds and pharmaceutical compositions disclosed herein for use in the prevention or treatment hyperproliferative diseases.

IL-6 often is often involved in STAT3 signaling. Independently of involving effects or not of STAT3 signaling, compounds and pharmaceutical compositions disclosed herein may be used for treatment or prevention of IL-6 mediated inflammation and/or autoimmune diseases and disorders, such as diseases and disorders related to the production of acute phase proteins. Another embodiment thus relates to compounds and pharmaceutical compositions disclosed herein for use in the prevention or treatment of IL-6 mediated inflammation and/or autoimmune diseases and disorders. Such diseases and disorders include, but are not limited to, atherosclerosis, diabetes type 2, dementia, osteoporosis, hypertension, coronary artery disease.

According to an embodiment, compounds and pharmaceutical compositions disclosed herein are used for the prevention or treatment of inflammatory and/or autoimmune diseases including, but not limited to, arthritis, Crohn's disease, ulcerative colitis, rheumatoid arthritis, inflammatory bowel diseases, asthma, allergy, e.g. Atopic dermatitis, systemic lupus erythematosus, uveitis and COPD. In addition, compounds of the invention may be used for the suppression of graft and transplant rejection, or for improved onset of the physiological functions of such grafts and transplants after transplantation.

According to an embodiment, compounds and pharmaceutical compositions disclosed herein are used for the prevention or treatment of inflammatory, autoimmune and neurodegenerative diseases affecting the CNS including, but not limited to, Parkinson's disease, Alzheimer's disease, multiple sclerosis, stroke and ischemia reperfusion injury.

According to an embodiment, compounds and pharmaceutical compositions disclosed herein are used for the prevention or treatment of chronic viral infections including, but not limited to, hepatitis C, herpes, infections caused by Kaposis Sarcoma-associated herpes virus (KSHV) and Epstein-Barr virus related infections.

According to an embodiment, compounds and pharmaceutical compositions disclosed herein are prevention or treatment of hyperproliferative diseases including, but not limited to, psoriasis.

When used in therapy, a pharmaceutical composition according embodiments herein may be administered to the patient in a pharmaceutically effective dose. By "pharmaceutically effective dose" is meant a dose that is sufficient to produce the desired effects in relation to the condition for which it is administered. The dose required for the therapeutic or preventive treatment of a particular disease or disorder will necessarily be varied depending on the host treated, the route of administration and the severity of the illness being treated. Further, the exact dose may be dependent on the activity of the compound, manner of administration, nature and severity of the disorder and/or disease and the general conditions, such as age and body weight of the patient.

A therapeutically effective amount for the practice of the present invention may be determined by one of ordinary skill in the art using known criteria including the age, weight and response of the individual patient, and interpreted within the context of the disease which is being treated or which is being prevented.

Evidently, compounds and pharmaceutical compositions disclosed herein may used for the manufacture of a medicament for use in such treatment and prevention as disclosed herein.

Similarly, compounds and compositions disclosed herein may obviously also be used in method for treating or preventing such diseases and disorders as have been disclosed herein. Such a method includes the step of administering an effective amount of the compound, or the pharmaceutical composition, to a subject in need for such treatment.

In the context of the present specification, the term "therapy" and "treatment" includes prevention or prophylaxis, unless there are specific indications to the contrary. The terms "therapeutic" and "therapeutically" should be construed accordingly.

According to an embodiment, treatment does also encompass pre-treatment, i.e. prophylactic treatment.

When used herein, "prevent/preventing" should not be construed to mean that a condition and/or a disease never might occur again after use of a compound or pharmaceutical composition according to embodiments disclosed herein to achieve prevention. Further, the term should neither be construed to mean that a condition not might occur, at least to some extent, after such use to prevent said condition. Rather, "prevent/preventing" is intended to mean that the condition to be prevented, if occurring despite such use, will be less severe than without such use.

Combination Therapy

As already described, pharmaceutical composition as disclosed herein may be used in therapy, the disclosed compounds, e.g. compounds according to formulae (I), (II) (X), (XI), (XII), and (XIII) or preferred selections thereof, acting as the principal therapeutic agent.

However, any of the disclosed compounds may also be supplemented with additional therapeutically active agent(s). According to an embodiment, the pharmaceutical composition does comprise one or more additional therapeutic agent(s). Preferably, the one or more additional therapeutic agents are selected among therapeutic agents having a mechanism of action that differ from the mechanism of action of the compound disclosed herein. An advantageous synergistic effect between the therapeutic agent and the compound disclosed herein may then occur, allowing a more effective combat of e.g. a disease than if only such a therapeutic agent or a compound as disclosed herein is used. The additional therapeutic agent may be an anti-cancer agent, e.g. chemotherapeutic agents. Further, also other therapeutic agents well known in the art, being effective for other diseases and conditions as described herein, may advantageously be used in combination with a compound as disclosed herein, in order to e.g. achieve a synergistic effect.

According to an embodiment, a compound or a pharmaceutical composition as disclosed herein is used in combination with other treatments or therapies, in particular cancer therapies, including chemotherapy, immunotherapy, radiation therapy, gene therapy, cell therapy and surgery. As an example, compounds disclosed herein may enhance anti-tumor immune mediated cytotoxicity or reverse resistance. Hence, synergistic effects between a compound disclosed herein, and another treatment or therapy or an immune mediated response, may favorably occur.

According to an embodiment, a pharmaceutical composition according to embodiments herein may be administered alone or in combination with other therapeutic agents. These agents may be incorporated as part of the same pharmaceutical composition or may be administered separately. It is well known in the art that a combination of mechanistically unrelated therapeutic agents in the same medicament may have beneficial effects in the treatment of conditions or diseases characterized by e.g. abnormal immune regulation, abnormal hematopoiesis, inflammation or oncogenesis.

Examples of other therapeutic agents include, but is not limited to, anti-cancer agents such as Abraxane, Abiraterone, Aldesleukin, Alemtuzumab, Aminolevulinic Acid, Anastrozole, Aprepitant, Arsenic Trioxide, Azacitidine, Bendamustine Hydrochloride, Bevacizumab, Bexarotene, Bortezomib, Bleomycin, Cabazitaxel, Capecitabine, Carboplatin, Cetuximab, Cisplatin, Clofarabine, Cyclophosphamide, Cytarabine, Dacarbazine, Dasatinib, Daunorubicin Hydrochloride, Decitabine, Degarelix, Denileukin Diftitox, Dexrazoxane Hydrochloride, Docetaxel, Doxorubicin Hydrochloride, Doxorubicin Hydrochloride Liposome, Eltrombopag Olamine, Enzalutamide, Epirubicin Hydrochloride, Erlotinib Hydrochloride, Etoposide, Etoposide Phosphate, Everolimus, Exemestane, Filgrastim, Fludarabine Phosphate, Fluorouracil, Fulvestrant, Gefitinib, Gemcitabine Hydrochloride, Ibritumomab Tiuxetan, Imatinib Mesylate, Imiquimod, Irinotecan Hydrochloride, Ixabepilone, Lapatinib Ditosylate, Lenalidomide, Letrozole, Leucovorin Calcium, Leuprolide Acetate, Liposomal Cytarabine, Methotrexate, Nelarabine, Nilotinib, Ofatumumab, Oxaliplatin, Paclitaxel, Palifermin, Palonosetron Hydrochloride, Panitumumab, Pazopanib Hydrochloride, Pegaspargase, Pemetrexed Disodium, Plerixafor, Pralatrexate, Raloxifene Hydrochloride, Rasburicase, Recombinant HPV Bivalent Vaccine, Recombinant HPV Quadrivalent Vaccine, Rituximab, Romidepsin, Romiplostim, Sipuleucel-T, Sorafenib Tosylate, Sunitinib Malate, Talc, Tamoxifen Citrate, Tasquinimod, TAK700, Temozolomide, Temsirolimus, Thalidomide, Topotecan Hydrochloride, Toremifene, Tositumomab and I 131 Iodine Tositumomab, Trastuzumab, Vincristine Sulfate, Vorinostat, ARN-509, ODM-201, custirsen, AT 101, cisplatin, abozantinib, dasatinib, MK2206, axitinib, saracatinib, tivantinib, linsitinib, GSK2636771, BKM120, Vorinostat, panobinostat, azacitidine, IPI-504, STA9090, lenalidomid, OGX-427, Zoledronic Acid and Xofigo, MED14736, tremelimumab, ipilimumab, Pembrolizumab, Nivolumab or the like.

When a compound according to embodiments disclosed herein is combined with at least another therapeutic agent, such as an anti-cancer agent, in a pharmaceutical composition, such as a medicament, a therapeutically effective dose of the pharmaceutical composition may comprise 1 to 10 times less than the respective established therapeutically effective dose of a component, i.e. a compound according to the invention or the therapeutic agent, when administered alone for prevention or treatment of the same disease or condition.

Accordingly, by combining a compound according to embodiments disclosed herein with another therapeutic agent, such as an anti-cancer agent, it may be possible to achieve synergistic effects compared to if only a compound according to the present invention, or the other therapeutic agent, were administrated alone.

For example compounds as disclosed herein, e.g. compounds according to formulae (I), (II) (X), (XI), (XII), and (XIII), may be used for reversing drug resistance and/or enhancing effects of anti cancer agents, thus offering the possibility of lowering the dose of the anticancer agent to avoid side-effects and/or enhancing the efficacy.

Pharmacological Tools

According to an embodiment, compounds disclosed herein are useful as pharmacological tools in the development and standardization of in-vitro and in-vivo test systems for the evaluation of other compounds with similar activity. Such in-vivo test systems include tests in laboratory animals such as cats, dogs, rabbits, monkeys, pigs, goats, guinea pigs, rats and mice. Furthermore, compounds disclosed herein may be used as molecular probes to identify and/or locate the target of their action, such as targets of relevance for STAT3 signaling, as well as employed as a diagnostic tool for diagnosis of a disease or condition in-vivo, ex-vivo or in-vitro, or as synthetic precursors to such probes.

Molecular probes are based on compounds disclosed herein, wherein one or several of the composing atoms have been enriched with a radioactive or by other means detectable isotope, and fluorescent compounds as well known to the one skilled in the art. Hence, compounds disclosed herein may include compounds wherein one or several atoms have been substituted with heavier isotopes, such as substitution of hydrogen for deuterium, carbon-12 for carbon-13 or carbon-14, and/or nitrogen-14 for nitrogen-15.

Although the present invention has been described above with reference to specific illustrative embodiments, it is not intended to be limited to the specific form set forth herein. Any combination of the above mentioned embodiments should be appreciated as being within the scope of the invention. Rather, the invention is limited only by the accompanying claims and other embodiments than the specific above are equally possible within the scope of these appended claims.

In the claims, the term "comprises/comprising" does not exclude the presence of other species or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality Methods of Preparation It is known that the hydroxyl group of galiellalactone is difficult to functionalize. This has limited modification of the hydroxyl group and thus the number of possible compounds available to elucidate the structure-activity relationship of structural modifications in that position ("Biosynthetic and Synthetic Studies of the Fungal Metabolite Galiellalactone", Martin Johansson, Doctoral Thesis, Lund University 2002; "The High-Intrinsic Diels-Alder Reactivity of (−)-Galiellalactone; Generating Four Quaternary Carbon Centers under Mild Conditions" Franz von Nussbaum, Roman Hanke, Thomas Fahrig, Jordi Benet-Buchholz, *Eur. J. Org. Chem.* 13, 2783-2790 (2004). Galiellalactone is sensitive to base treatment so alkylation of the tertiary hydroxyl group (i.e. O-alkylation) requires neutral conditions. Neutral O-alkylation may be achieved by treatment with Ag2O and MeI but this severely constrains the number and type of alkylation reagents that can be used. A more efficient way of synthesizing hydroxyl-modified (O-modified) galeillalactone analogs would be highly desired.

In contrast to O-alkylation, acylation of the hydroxyl group (i.e. O-acylation) can be achieved without needing a base. Galiellalactone may be treated with an excess of acetylchloride or actetic acid anhydride to give O-acetylated galiellalactone. However, O-acetylated galiellalactone is unstable towards nuceleophiles and nuceleophilic addition to the double bond will lead to elimination of acetate.

The present inventors have surprisingly found that when O-acetylated galiellalactone is treated with a primary amine the acetate is substituted by the amine in an unprecedented substitution reaction on a tertiary carbon with complete retention of stereochemistry. For instance, the reaction of O-acetylated galiellalactone with benzylamine is as follows:

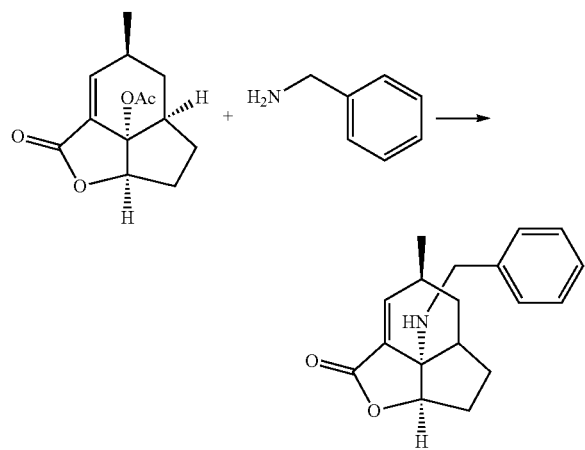

Although the formed amine adducts display some cellular activity, the adducts are unstable towards thiols such as cysteine, thereby rendering them less interesting as drug leads.

Without wishing to be bound by theory, it is believed that under physiological conditions the amine is protonated and acts as a leaving group. Given the reactivity of the amine adducts, it was expected that treatment of O-acetylated galiellalactone with alcohols would provide more stable O-alkylated galiellalactone analogs. However, the present inventors found that treatment with primary alcohols alone did not result in any desired products as O-acetylated galiellalactone was unreactive towards the alcohols. It was then surprisingly found that adding 0.1 equivalents of 4-dimethylaminopyridine (DMAP) during treatment of O-acetylated galiellalactone with an alcohol resulted in the clear substitution of the acetate group and that this reaction could be expanded to a wide variety of primary alcohols containing different functional groups. This unprecedented substitution reaction at a tertiary carbon atom of galiellalactone without any involvement of cationic intermediates allows for the synthesis of the novel galiellalactone-based STAT3 inhibitors with the improved properties disclosed herein.

Accordingly, another embodiment relates to a process for preparing a compound disclosed herein, e.g. compounds according to formulae (I), (II) (X), (XI), (XII), and (XIII) or preferred selections thereof, as a free base, acid, or salts thereof. Further, additionally embodiments relate to synthetic intermediates, which are useful in the synthesis of a compound of formulae (I), (II) (X), (XI), (XII), or (XIII) as a free base, acid, or salts thereof. Specific and generic examples of such intermediates are given below.

In another embodiment there is provided the use of a non-nucleophilic base with nucleophilic catalytic activity, e.g. a tertiary amine, in the reaction of an unsubstituted or substituted galiellalactone-O-L with an alcohol to form an unsubstituted or substituted galiellalactone ether, wherein O-L is a leaving group.

In some embodiments the L is selected from the group consisting of alkanoyl, aroyl, sulfonyl, and phosphonyl.

In some embodiments the L is selected from the group consisting of —COCH₃, —COPh, —SO₂CF₃, —SO₂Me, —SO₂tolyl, —SO₂(p-bromophenyl), —SO₂(2-NO₂-phenyl), —SO₂(4-NO₂-phenyl), —NO₂, and —PO(OH)₂.

In some embodiments the galiellalactone-O-L is substituted with 1, 2, 3, 4, or 5 substituents selected from the group consisting of C1-5 alkyl, C1-5 fluoroalkyl, halo, cyano, nitro, —OH, OC1-5 alkyl, C1-5 alkyleneOH, C1-5 alkyleneOC1-5 alkyl, C3-8 non-aromatic carbocycle, OC1-5 fluoroalkyl, C1-3 alkyleneOC1-5 fluoroalkyl, OC(O)C1-5 alkyl, C1-3 alkyleneOC(O)C1-5 alkyl, OC2-3 alkyleneNH2, OC2-3 alkyleneNH(C1-5 alkyl), OC2-3 alkyleneN(C1-5 alkyl)2 in which the C1-5 alkyl may be the same or different, —NH2, —NH(C1-5 alkyl), C1-3 alkyleneNH2, C1-3 alkyleneNH(C1-5 alkyl), —N(C1-5 alkyl)2 in which the C1-5 alkyl may be the same or different, C1-3 alkyleneN(C1-5 alkyl)2 in which the C1-5 alkyl may be the same or different, NHC(O)C1-5 alkyl, N(C1-5 alkyl)C(O)C1-5 alkyl, C1-3 alkyleneNHC(O)C1-5 alkyl, C1-3 alkyleneN(C1-5 alkyl)C(O)C1-5 alkyl, NHaryl, C1-3 alkyleneNHaryl, NHheteroaryl, C1-3 alkyleneNHheteroaryl, aryl, C1-3 alkylene-aryl, heteroaryl, C1-3 alkylene-heteroaryl, —SH, —SC1-5 alkyl, C1-5 alkylene-SH, C1-5 alkylene-SC1-5 alkyl, SC1-5 fluoroalkyl, C1-5 alkyleneSC1-5 fluoroalkyl, SO2C1-5 alkyl, C1-5 alkylene-SO2C1-5 alkyl, SO2C1-5 fluoroalkyl, C1-5 alkylene-SO2C1-5 fluoroalkyl, SO2NH2, SO2NH(C1-5 alkyl), SO2N(C1-5 alkyl)2 in which the C1-5 alkyl may be the same or different, C1-5 alkyleneSO2NH2, C1-5 alkyleneSO2NH(C1-5 alkyl), C1-5 alkyleneSO2N(C1-5 alkyl)2 in which the C1-5 alkyl may be the same or different, SO2NHaryl, C1-5 alkyleneSO2NHaryl, SO2N(C1-5 alkyl)aryl, and C1-5 alkyleneSO2N(C1-5 alkyl)aryl.

In some embodiments the alcohol is selected from the group consisting of a primary alcohol, secondary alcohol, HO—(CH₂)₁₋₃-aryl, HO—(CH₂)₁₋₃-heteroaryl, HO—(CH₂)₁₋₃-non-aromatic carbocycle, and HO—(CH₂)₁₋₃-non-aromatic heterocycle, wherein the alcohol may be unsubstituted or substituted with 1, 2, or 3 substituents selected from the group consisting of C1-5 alkyl, C1-5 haloalkyl, halo, cyano, —CH₂-cyano, —OH, OC1-5 alkyl, C1-8 alkyleneOC1-5 alkyl, O-aryl, C1-8 alkylene-O-aryl, —SH, SC1-5 alkyl, SO₂H, SO₂C1-5 alkyl, C1-3 alkyleneSO₂H, C1-3 alkyleneSO₂C1-5 alkyl, OC1-3 fluroroalkyl, C1-3 alkyleneOC1-3 fluroroalkyl, NH2, NH(C1-3 alkyl), C1-3 alkylene-NH2, C1-3 alkyleneNH(C1-3 alkyl), N(C1-5 alkyl)₂ in which the C1-5 alkyl may be the same or different, C1-3 alkyleneN(C1-5 alkyl)₂ in which the C1-5 alkyl may be the same or different, C(O)OH, C(O)OC1-5 alkyl, C1-3 alkyleneC(O)OH, C1-3 alkyleneC(O)OC1-5 alkyl, OC(O)H, OC(O)C1-5 alkyl, C1-3 alkyleneOC(O)H, C1-3 alkyleneOC(O)C1-5 alkyl, NHC(O)H, NHC(O)C1-5 alkyl, N(C1-3 alkyl)C(O)H, N(C1-3 alkyl)C(O)C1-5 alkyl, C1-3 alkyleneNHC(O)H, C1-3 alkyleneNHC(O)C1-5 alkyl, C1-3 alkyleneN(C1-3 alkyl)C(O)H, C1-3 alkyleneN(C1-3 alkyl)C(O)C1-5 alkyl, C(O)NH2, C(O)NH(C1-3 alkyl), C1-3 alkyleneC(O)NH2, C1-3 alkyleneC(O)NH(C1-3 alkyl), C(O)N(C1-5 alkyl)₂, in which the C1-5 alkyl may be the same or different, C1-3 alkyleneC(O)N(C1-5 alkyl)₂, in which the C1-5 alkyl may be the same or different, nitro, C(O)H, C(O)C1-C5 alkyl, NHSO2C1-C3 alkyl, N(C1-C3 alkyl)SO2C1-C3 alkyl, NHSO2C1-C3 fluoroalkyl, N(C1-C3 alkyl)SO2C1-C3 fluoroalkyl, OC2-C3alkyleneNH2, OC2-C3alkyleneNH(C1-C3 alkyl), and OC2-C3alkyleneN(C1-C3 alkyl)₂ in which the C1-3 alkyl may be the same or different.

In an embodiment the galiellalactone ether is a compound according to any one of formulae (I), (II) (X), (XI), (XII), or (XIII) as described above.

In some embodiments the non-nucleophilic base is a tertiary amine selected from the group consisting of an arylamine, a heteroarylamine, 1,4-Diazabicyclo[2.2.2]octane (DABCO), 1,8-Diazabicyclo[5.4.0]undec-7-ene (DBU), 1,5-Diazabicyclo[4.3.0]non-5-ene (DBN), and quinuclidine.

According to a particular embodiment the tertiary amine is 4-dimethylaminopyridine (DMAP).

Throughout the following description of such processes it is to be understood that, where appropriate, suitable protecting groups will be attached to, and subsequently removed from, the various reactants and intermediates in a manner that will be readily understood by one skilled in the art of organic synthesis. Conventional procedures for using such protecting groups, as well as examples of suitable protecting groups, are well known within the art. Further such procedures and groups are described in the literature, such as in "Protective Groups in Organic Synthesis", 3rd ed., T. W. Green, P. G. M. Wuts, Wiley-Interscience, New York (1999).

It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis.

Examples of transformations are given below, and it is to be understood that the described transformations are not limited only to the generic groups or substituents for which the transformations are exemplified.

Starting materials for the synthesis of compounds of formula (II) described above are obtained by the procedures disclosed in PCT/EP2015/054754.

References and descriptions on other suitable transformations are for example given in "Comprehensive Organic Transformations—A Guide to Functional Group Preparations", 2nd ed., R. C. Larock, Wiley-VCH, New York (1999). References and descriptions of other suitable reactions are described in textbooks of organic chemistry well known to the one skilled in the art, such as "March's Advanced Organic Chemistry", 5th ed., M. B. Smith, J. March, John Wiley & Sons (2001) or, "Organic Synthesis", 2nd ed., M. B. Smith, McGraw-Hill, (2002).

In the various schemes given below, generic groups, such as R-groups, have the same representation as given above herein, if not specifically defined.

Method of Preparation of Final Compounds of Formula I by Coupling of Intermediates II and III (Scheme 1)

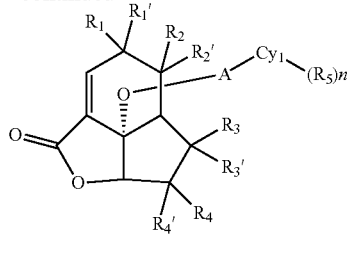

I

Formation of compounds of formula I may be accomplished by coupling of II and III in the presence of a suitable base, e.g. DMAP, where L is e.g. —SO$_2$CF$_3$, —Ac, —SO$_2$Me, —SO$_2$tolyl, under ambient conditions.

Compounds of formula III are commercially available.

The synthesis of compounds of formula II where L is —Ac has been described in "Biosynthetic and Synthetic Studies of the Fungal Metabolite Galiellalactone", Martin Johansson, Doctoral Thesis, Lund University 2002 and in "The High-Intrinsic Diels-Alder Reactivity of (−)-Galiellalactone; Generating Four Quaternary Carbon Centers under Mild Conditions" Franz von Nussbaum, Roman Hanke, Thomas Fahrig, Jordi Benet-Buchholz, *Eur. J Org. Chem.* 13, 2783-2790 (2004). Examples of compounds of formula II, include, but are not limited to:

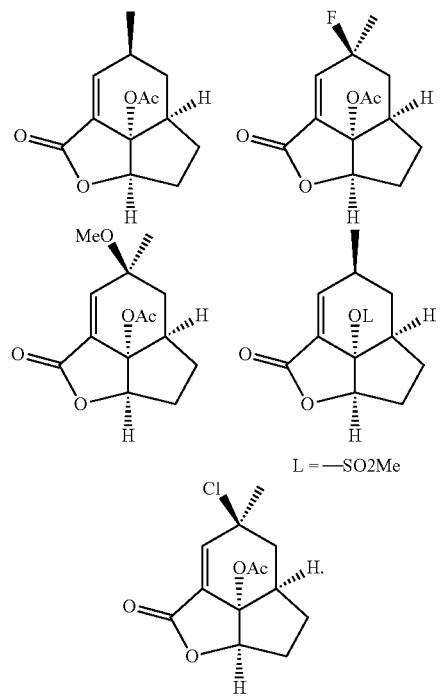

L = —SO2Me

Alternate Method of Preparation of Final Compounds of Formula I by Alkylation of Intermediates IV by V (Scheme 2)

Scheme 1

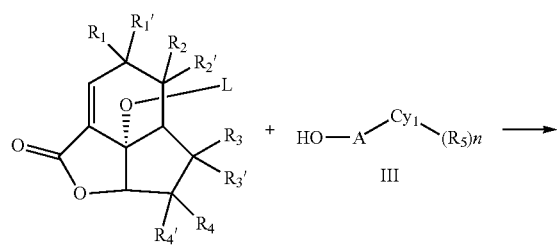

II

Scheme 2

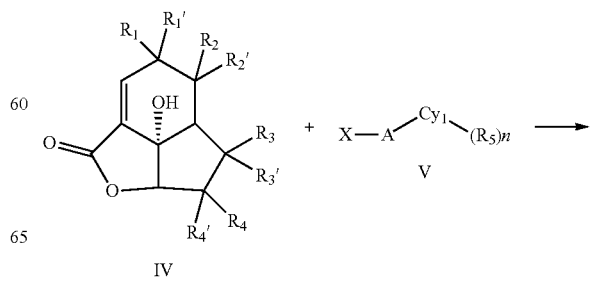

IV

-continued

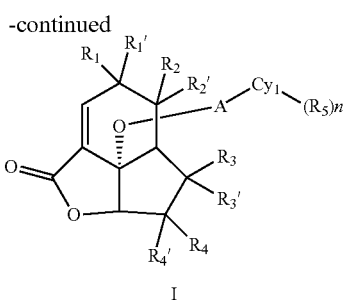

I

Compounds of formula IV can be alkylated by compounds of formula V (where X is a suitable leaving group e.g. Cl, Br, tosylate, mesylate, triflate) in the presence of a silver salt (e.g. Ag$_2$O). If both R$_1$ and R$_1$' are not H then IV can be treated with a suitable base, e.g. NaH or LDA, prior to treatment with compounds of formula V to obtain products of formula I.

Method of Preparation of Intermediates of Formula IV as Used in Scheme 2 Above (Scheme 3)

Scheme 3

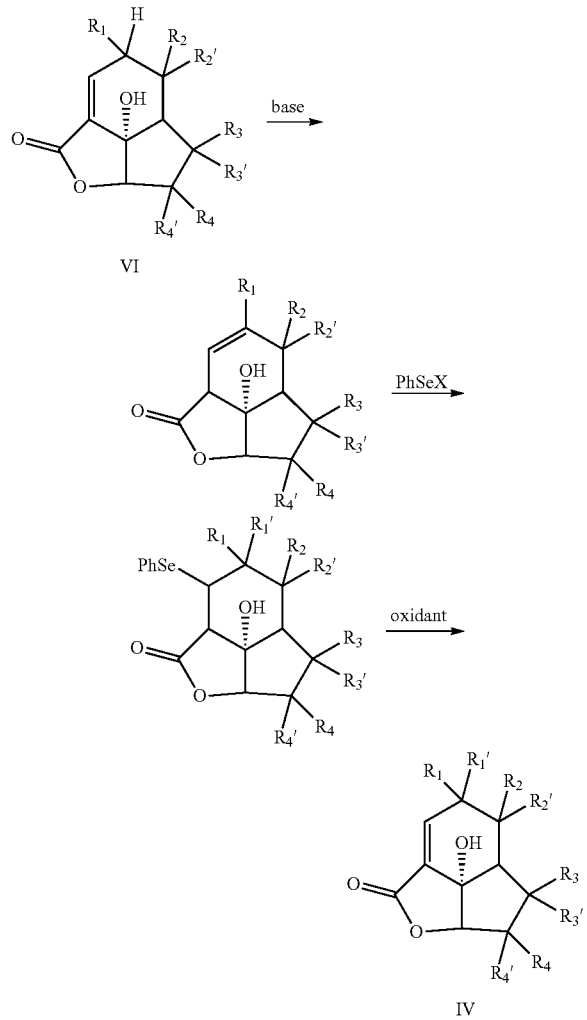

The sequence of steps leading to introduction of the R$_1$' substituent into the intermediates of formula IV is shown in scheme 3. Compounds of formula IV may be prepared from compounds of formula VI by a sequence of base induced double bond isomerisation, treatment with a suitable selenylation reagent and oxidative elimination to introduce the double bond. The base may be DBU, DMAP, TEA, or KOtBu and the selenylation reagent, PhSeX, maybe PhSeCl, PhSeCN, PhSe-phthalimide alone or in the presence of a suitable source of R$_1$' such as MeOH, TEA-HF, NH2C(O)OEt, water or acetic acid with or without a Lewis acid catalyst. Examples of R$_1$' substituents on intermediates of formula IV in Scheme 3 that may be introduced by this sequence include F, Cl, OMe, and OH.

A preferred example of a compound according to formula IV is

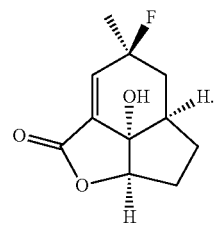

EXAMPLES

Abbreviations
DMF N,N'-Dimethylformamide
THF Tetrahydrofurane
DMSO Dimethylsulfoxide
sat Saturated aqueous solution
Boc t-Butoxycarbonyl
TFA Trifluoroacetic acid
TEA Triethylamine
DBU 1,8-Diazabicycloundec-7-ene
DMAP 4-Dimethylaminopyridine
DIPEA N,N-Diisopropylethylamine
DABCO 1,4-Diazabicyclo[2.2.2]octane
DBN 1,5-Diazabicyclo[4.3.0]non-5-ene
h hour
r.t. room temperature
RC Remaining contraction
equiv equivalents
quant quantative
aq aqueous
Ph phenyl
tol toluene
pyr pyridine General Methods All materials were obtained from commercial sources and were used without further purification unless otherwise noted. THF was distilled from sodium and benzophenone. NMR spectra (in CDCl$_3$, CD$_3$OD or DMSO-d6) were recorded on a Bruker DRX 400 or on a Bruker Ultrashield 400 spectrometer at 400 MHz. All chemical shifts are in ppm on the delta-scale (δ) relative to TMS using the residual CHCl$_3$ peak in CDCl$_3$, or the residual CD$_2$HOD peak in CD$_3$OD, or the residual CD$_3$SOCD$_2$H peak in (CD$_3$)$_2$SO as internal standard (7.26, 3.31 or 2.50 ppm respectively relative to TMS) and the fine splitting of the signals as appearing in the recordings (s: singlet, d: doublet, t: triplet, q: quartet, m: multiplet, br: broad signal). Flash chromatography was performed using 60 Å 35-70 μm Davisil silica gel. TLC analyses were made on Silica Gel 60 F254 (Merck) plates and visualised under a 254/365 nm UV-lamp.

Techniques for purification of intermediates and final products include for example, straight and reversed phase chromatography on column or rotating plate, size exclusion chromatography, recrystallisation, distillation and liquid-liquid or solid-liquid extraction, which will be readily understood by the one skilled in the art.

The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures.

The terms "flash chromatography" or "flash column chromatography" shall mean preparative chromatography on silica using an organic solvent, or mixtures thereof, as mobile phase.

General Procedure for the Synthesis of Galiellalactone Ethers 7b (Scheme 4)

Scheme 4

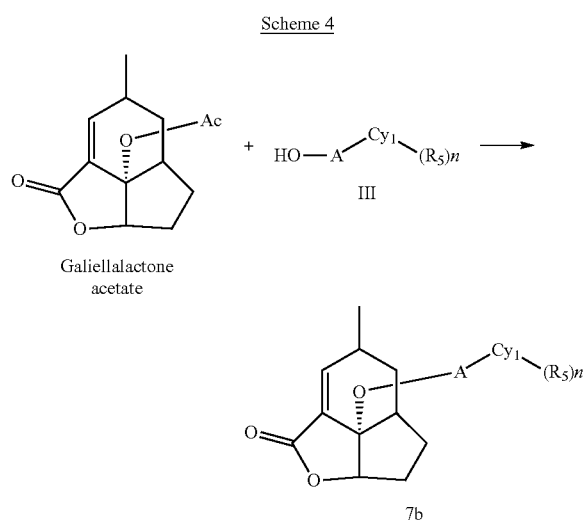

Galiellalactone acetate (1.0 eq.) and N, N'-dimethylaminopyridine (1.1 eq.) were suspended in anhydrous CH$_2$Cl$_2$. The corresponding alcohol (III) (1.1 eq.) was added to the mixture and stirring continued for 18 h. Water was added to the mixture and the product extracted with EtOAc, dried over MgSO$_4$ and concentrated. The crude product was purified by flash chromatography (solvent system, yield and analytical data given for each compound).

Examples 1 to 25 below are compounds of 7b that were prepared using commercially available alcohols (III) and the procedure in scheme 4.

Example 1

(4R,5aS,7aS,7bR)-5,5a,6,7,7a,7b-hexahydro-7b-[(6-methyl-3-pyridinyl)methoxy]-4-methyl-indeno[1,7-bc]furan-2(4H)-one

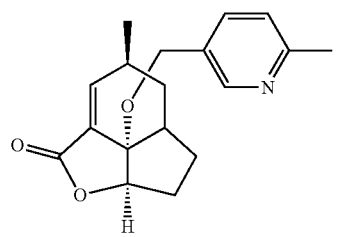 [SMILES: Cc1ccc(CO[C@]23C4=C[C@@H](C)CC2CC[C@H]3OC4=O)cn1]

heptane/EtOAc 4:6. Yield 53%

$^1$H NMR (400 MHz, CDCl$_3$) δ 8.41 (m, 1H), 7.50 (m, 1H), 7.21 (m, 1H), 7.15 (m, 1H), 4.95 (m, 1H), 4.36 (s, 2H), 2.61 (m, 1H), 2.56 (s, 3H), 2.53 (m, 1H), 2.26 (m, 1H), 2.10 (m, 1H), 1.89 (m, 1H), 1.83 (m, 1H), 1.22 (m, 3H), 1.18 (m, 1H), 0.98 (m, 1H).

Example 2

(4R,5aS,7aS,7bR)-5,5a,6,7,7a,7b-hexahydro-7b-[(6-phenoxy-3-pyridinyl)methoxy]-4-methyl-indeno[1,7-bc]furan-2(4H)-one

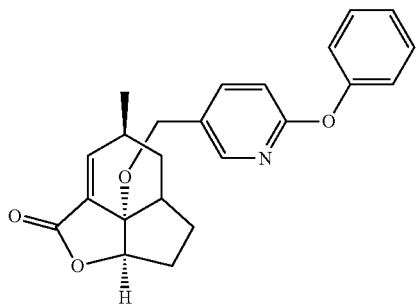 [SMILES: C[C@@H]1C=C2C(=O)O[C@@H]3CCC(C1)[C@]23OCc1ccc(Oc2ccccc2)nc1]

heptane/EtOAc 4:6. Yield 72%

$^1$H NMR (500 MHz, CDCl$_3$) δ 8.10 (m, 1H), 7.59 (m, 1H), 7.39 (m, 2H), 7.21 (m, 1H), 7.20 (m, 1H), 7.10 (m, 2H), 4.95 (m, 1H), 4.33 (s, 2H), 2.58 (m, 1H), 2.55 (m, 1H), 2.25 (m, 1H), 2.09 (m, 1H), 1.87 (m, 1H), 1.83 (m, 1H), 1.21 (m, 3H), 1.18 (m, 1H), 0.98 (m, 1H).

Example 3

(4R,5aS,7aS,7bR)-5,5a,6,7,7a,7b-hexahydro-7b-[2-(3-pyridinyl)-ethoxy]-4-methyl-indeno[1,7-bc]furan-2(4H)-one

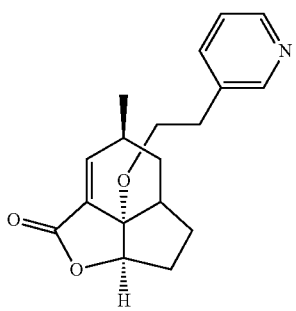 [SMILES: C[C@@H]1C=C2C(=O)O[C@@H]3CCC(C1)[C@]23OCCc1cccnc1]

heptane/EtOAc 4:6. Yield 67%.

$^1$H NMR (500 MHz, CDCl$_3$) δ 8.43 (m, 2H), 7.52 (m, 1H), 7.23 (m, 1H), 7.05 (m, 1H), 4.72 (m, 1H), 3.50 (m, 2H), 2.79 (m, 2H), 2.41 (m, 1H), 2.23 (m, 1H), 2.11 (m, 1H), 1.98 (m, 1H), 1.78 (m, 1H), 1.74 (m, 1H), 1.10 (m, 3H), 1.08 (m, 1H), 0.87 (m, 1H).

Example 4

(4R,5aS,7aS,7bR)-5,5a,6,7,7a,7b-hexahydro-7b-[(5-methyl-2-pyrazinyl)methoxy]-4-methyl-indeno[1,7-bc]furan-2(4H)-one

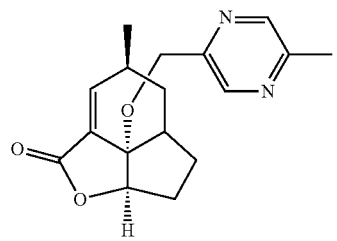 [SMILES: Cc1cnc(CO[C@]23C4=C[C@@H](C)CC2CC[C@H]3OC4=O)cn1]

heptane/EtOAc 4:6. Yield 64%
$^1$H NMR (500 MHz, CDCl$_3$) δ 8.48 (s, 1H), 8.39 (s, 1H), 7.20 (m, 1H), 4.97 (m, 1H), 4.50 (s, 2H), 2.61 (m, 1H), 2.59 (m, 1H), 2.25 (m, 1H), 2.10 (m, 1H), 2.07 (s, 3H), 1.88 (m, 1H), 1.82 (m, 1H), 1.19 (m, 3H), 1.18 (m, 1H), 0.97 (m, 1H).

Example 5

(4R,5aS,7aS,7bR)-5,5a,6,7,7a,7b-hexahydro-7b-[(4-methoxy-2-pyridinyl)methoxy]-4-methyl-indeno[1,7-bc]furan-2(4H)-one

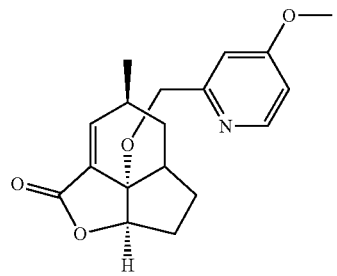 [SMILES: COc1ccnc(CO[C@]23C4=C[C@@H](C)CC2CC[C@H]3OC4=O)c1]

100% EtOAc. Yield 42%.
$^1$H NMR (500 MHz, CDCl$_3$) δ 8.36 (m, 1H), 7.17 (m, 1H), 6.88 (m, 1H), 6.72 (m, 1H), 4.95 (m, 1H), 4.48 (s, 2H), 3.86 (s, 3H), 2.65 (m, 1H), 2.62 m, 1H), 2.27 (m, 1H), 2.10 (m, 1H), 1.90 (m, 1H), 1.80 (m, 1H), 1.23 (m, 1H), 1.20 (m, 3H), 0.99 (m, 1H).

Example 6

(4R,5aS,7aS,7bR)-5,5a,6,7,7a,7b-hexahydro-7b-[(6-methoxycarbonyl-2-pyridinyl)methoxy]-4-methyl-indeno[1,7-bc]furan-2(4H)-one

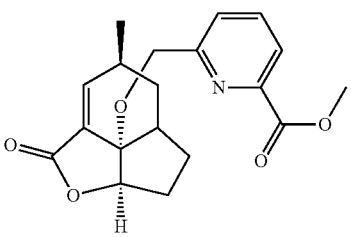 [SMILES: COC(=O)c1cccc(CO[C@]23C4=C[C@@H](C)CC2CC[C@H]3OC4=O)n1]

heptane/EtOAc 4:6. Yield 60%.
$^1$H NMR (500 MHz, CDCl$_3$) δ 8.01 (m, 1H), 7.84 (m, 1H), 7.59 (m, 1H), 7.16 (m, 1H), 4.94 (m, 1H), 4.62 (s, 2H), 3.98 (s, 3H), 2.62 (m, 2H), 2.25 (m, 1H), 2.08 (m, 1H), 1.89 (m, 1H), 1.78 (m, 1H), 1.22 (m, 1H), 1.18 (m, 3H), 0.99 (m, 1H).

Example 7

(4R,5aS,7aS,7bR)-5,5a,6,7,7a,7b-hexahydro-7b-[(2-methoxy-3-pyridinyl)methoxy]-4-methyl-indeno[1,7-bc]furan-2(4H)-one

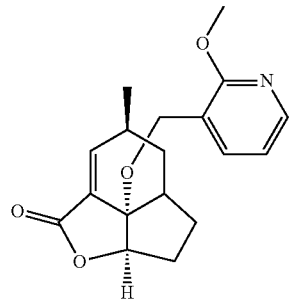 [SMILES: COc1ncccc1CO[C@]12C3=C[C@@H](C)CC1CC[C@H]2OC3=O]

Heptane/EtOAc 7:3. Yield 76%
$^1$H NMR (500 MHz, CDCl$_3$) δ 8.08 (m, 1H), 7.58 (m, 1H), 7.19 (m, 1H), 6.86 (m, 1H), 4.98 (m, 1H), 4.35 (s, 2H), 3.93 (s, 3H), 2.63 (m, 1H), 2.58 (m, 1H), 2.26 (m, 1H), 2.09 (m, 1H), 1.89 (m, 1H), 1.84 (m, 1H), 1.21 (m, 3H), 1.17 (m, 1H), 0.97 (m, 1H).

Example 8

(4R,5aS,7aS,7bR)-5,5a,6,7,7a,7b-hexahydro-7b-[(2-methyl-3-pyridinyl)methoxy]-4-methyl-indeno[1,7-bc]furan-2(4H)-one

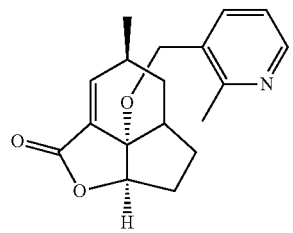 [SMILES: Cc1ncccc1CO[C@]12C3=C[C@@H](C)CC1CC[C@H]2OC3=O]

heptane/EtOAc 4:6. Yield 80%.
$^1$H NMR (500 MHz, CDCl$_3$) δ 8.42 (m, 1H), 7.58 (m, 1H), 7.22 (m, 1H), 7.12 (m, 1H), 4.95 (m, 1H), 4.39 (m, 1H), 4.35 (m, 1H), 2.60 (m, 1H), 2.57 (m, 1H), 2.49 (s, 3H), 2.27 (m, 1H), 2.10 (m, 1H), 1.89 (m, 1H), 1.83 (m, 1H), 1.22 (m, 3H), 1.18 (m, 1H), 1.02 (m, 1H).

Example 9

(4R,5aS,7aS,7bR)-5,5a,6,7,7a,7b-hexahydro-7b-[(6-[(2,2-dimethyl-1-oxopropyl)amino]-3-pyridinyl]methoxy]-4-methyl-indeno[1,7-b]c furan-2(4H)-one

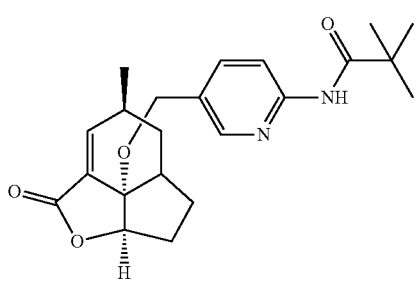 [SMILES: C[C@@H]1C=C2C(=O)O[C@@H]3CCC(C1)[C@]23OCc1ccc(NC(=O)C(C)(C)C)nc1]

heptane/EtOAc 4:6. Yield 75%.
$^1$H NMR (500 MHz, CDCl$_3$) δ 8.22 (m, 1H), 8.14 (m, 1H), 8.06 (brs, 1H), 7.61 (m, 1H), 7.20 (m, 1H), 4.94 (m, 1H), 4.34 (s, 2H), 2.60 (m, 1H), 2.55 (m, 1H), 2.26 (m, 1H), 2.09 (m, 1H), 1.88 (m, 1H), 1.82 (m, 1H), 1.32 (s, 9H), 1.21 (m, 3H), 1.17 (m, 1H), 0.98 (m, 1H).

Example 10

(4R,5aS,7aS,7bR)-5,5a,6,7,7a,7b-hexahydro-7b-[(6-trifluoromethyl-3-pyridinyl)methoxy]-4-methyl-indeno[1,7-bc]furan-2(4H)-one

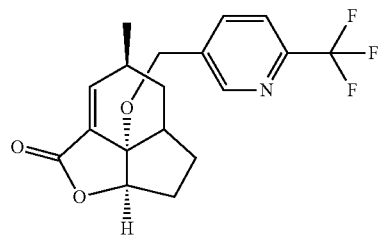 [SMILES: C[C@@H]1C=C2C(=O)O[C@@H]3CCC(C1)[C@]23OCc1ccc(C(F)(F)F)nc1]

heptane/EtOAc 7:3. Yield 40%

$^1$H NMR (500 MHz, CDCl$_3$) δ 8.64 (m, 1H), 7.78 (m, 1H), 7.66 (m, 1H), 7.23 (m, 1H), 4.95 (m, 1H), 4.49 (s, 2H), 2.59 (m, 1H), 2.58 (m, 1H), 2.28 (m, 1H), 2.13 (m, 1H), 1.92 (m, 1H), 1.84 (m, 1H), 1.23 (m, 1H), 1.22 (m, 3H), 1.03 (m, 1H).

Example 11

(4R,5aS,7aS,7bR)-5,5a,6,7,7a,7b-hexahydro-7b-[(2-amino-3-pyridinyl)methoxy]-4-methyl-indeno[1,7-bc]furan-2(4H)-one

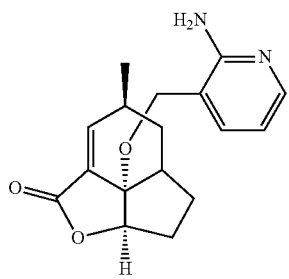 [SMILES: C[C@@H]1C=C2C(=O)O[C@@H]3CCC(C1)[C@]23OCc1cccnc1N]

100% EtOAc. Yield 75%

$^1$H NMR (500 MHz, CDCl$_3$) δ 7.99 (m, 1H), 7.29 (m, 1H), 7.19 (m, 1H), 6.63 (m, 1H), 5.01 (brs, 2H), 4.89 (m, 1H), 4.34 (m, 2H), 2.57 (m, 1H), 2.53 (m, 1H), 2.25 (m, 1H), 2.07 (m, 1H), 1.86 (m, 1H), 1.80 (m, 1H), 1.21 (m, 3H), 1.17 (m, 1H), 1.02 (m, 1H).

Example 12

(4R,5aS,7aS,7bR)-5,5a,6,7,7a,7b-hexahydro-7b-[(6-phenyl-3-pyridinyl)methoxy]-4-methyl-indeno[1,7-bc]furan-2(4H)-one

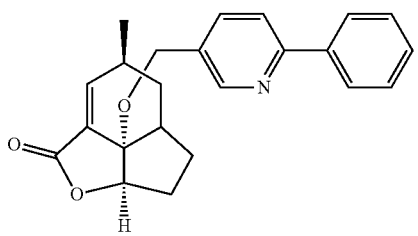 [SMILES: C[C@@H]1C=C2C(=O)O[C@@H]3CCC(C1)[C@]23OCc1ccc(-c2ccccc2)nc1]

heptane/EtOAc 7:3. Yield 62%

$^1$H NMR (500 MHz, CDCl$_3$) δ 8.60 (m, 1H), 7.98 (m, 2H), 7.71 (m, 1H), 7.66 (m, 1H), 7.47 (m, 2H), 7.42 (m, 1H), 7.23 (m, 1H), 4.99 (m, 1H), 4.44 (m, 2H), 2.65 (m, 1H), 2.61 (m, 1H), 2.28 (m, 1H), 2.13 (m, 1H), 1.91 (m, 1H), 1.87 (m, 1H), 1.23 (m, 3H), 1.21 (m, 1H), 1.00 (m, 1H).

Example 13

(4R,5aS,7aS,7bR)-5,5a,6,7,7a,7b-hexahydro-7b-[(2,6-dimethoxy-3-pyridinyl)methoxy]-4-methyl-indeno[1,7-bc]furan-2(4H)-one

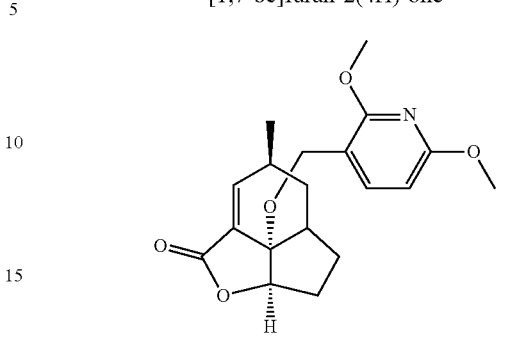

heptane/EtOAc 9:1. Yield 65%

$^1$H NMR (500 MHz, CDCl$_3$) δ 7.44 (m, 1H), 7.18 (m, 1H), 6.26 (m, 1H), 4.99 (m, 1H), 4.28 (s, 2H), 3.92 (s, 3H), 3.90 (s, 3H), 2.65 (m, 1H), 2.55 (m, 1H), 2.24 (m, 1H), 2.06 (m, 1H), 1.85 (m, 1H), 1.84 (m, 1H), 1.21 (m, 3H), 1.15 (m, 1H), 0.94 (m, 1H).

Example 14

(4R,5aS,7aS,7bR)-5,5a,6,7,7a,7b-hexahydro-7b-[7-(3,4-dihydro-4-methyl 2H-Pyrido[3,2-b]-1,4-oxazinyl)methoxy]-4-methyl-indeno[1,7-bc]furan-2(4H)-one

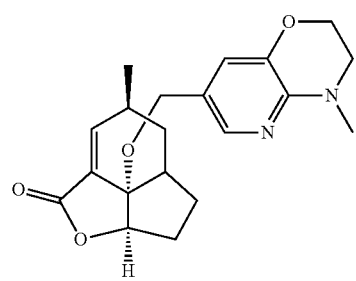 [SMILES: C[C@@H]1C=C2C(=O)O[C@@H]3CCC(C1)[C@]23OCc1cnc2c(c1)OCCN2C]

heptane/EtOAc 4:6. Yield 60%

$^1$H NMR (500 MHz, CDCl$_3$) δ 7.64 (m, 1H), 7.19 (m, 1H), 6.82 (m, 1H), 4.95 (m, 1H), 4.22 (m, 2H), 4.18 (m, 2H), 3.42 (m, 2H), 3.10 (s, 3H), 2.61 (m, 1H), 2.52 (m, 1H), 2.23 (m, 1H), 2.06 (m, 1H), 1.83 (m, 1H), 1.86 (m, 1H), 1.20 (m, 3H), 1.14 (m, 1H), 0.93 (m, 1H).

Example 15

(4R,5aS,7aS,7bR)-5,5a,6,7,7a,7b-hexahydro-7b-[(6-(N-morpholino)-3-pyridinyl)methoxy]-4-methyl-indeno[1,7-bc]furan-2(4H)-one

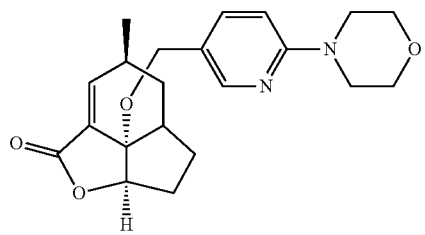 [SMILES: C[C@@H]1C=C2C(=O)O[C@@H]3CCC(C1)[C@]23OCc1ccc(N2CCOCC2)nc1]

heptane/EtOAc 4:6 Yield 68%

$^1$H NMR (500 MHz, CDCl$_3$) δ 8.08 (m, 1H), 7.40 (m, 1H), 7.20 (m, 1H), 6.61 (m, 1H), 4.95 (m, 1H), 4.26 (m, 1H), 4.24 (m, 1H), 3.80 (m, 4H), 3.48 (m, 4H), 2.60 (m, 1H), 2.52 (m, 1H), 2.23 (m, 1H), 2.07 (m, 1H), 1.86 (m, 1H), 1.82 (m, 1H), 1.20 (m, 3H), 1.16 (m, 1H), 0.95 (m, 1H).

Example 16

(4R,5aS,7aS,7bR)-5,5a,6,7,7a,7b-hexahydro-7b-[(6-(N-pyrrolidinyl)-3-pyridinyl)methoxy]-4-methyl-indeno[1,7-bc]furan-2(4H)-one

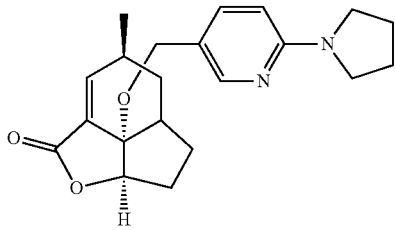 [SMILES: C[C@@H]1C=C2C(=O)O[C@@H]3CCC(C1)[C@]23OCc1ccc(N2CCCC2)nc1]

heptane/EtOAC 4:6. Yield 65%
$^1$H NMR (500 MHz, CDCl$_3$) δ 8.03 (m, 1H), 7.32 (m, 1H), 7.19 (m, 1H), 6.32 (m, 1H), 4.95 (m, 1H), 4.21 (s, 2H), 3.43 (m, 4H), 2.61 (m, 1H), 2.52 (m, 1H), 2.22 (m, 1H), 2.06 (m, 1H), 1.99 (m, 4H), 1.82 (m, 2H), 1.20 (d, J=7.2 Hz, 3H), 1.14 (m, 1H), 0.93 (m, 1H)

Example 17

(4R,5aS,7aS,7bR)-5,5a,6,7,7a,7b-hexahydro-7b-[(4-pyridinyl)methoxy]-4-methyl-indeno[1,7-bc]furan-2(4H)-one

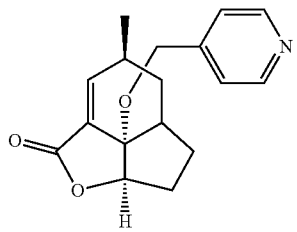 [SMILES: C[C@@H]1C=C2C(=O)O[C@@H]3CCC(C1)[C@]23OCc1ccncc1]

heptane/EtOAc 7:3. Yield 72%.
$^1$H NMR (500 MHz, CDCl$_3$) δ 8.52 (m, 2H), 7.22 (m, 2H), 7.19 (m, 1H), 4.91 (m, 1H), 4.40 (s, 2H), 2.60 (m 1H); 2.58 (m 1H), 2.27 (m, 1H), 2.10 (m, 1H), 1.89 (m, 1H), 1.81 (m, 1H), 1.20 (m, 3H), 1.20 (m, 1H), 1.00 (m, 1H).

Example 18

(4R,5aS,7aS,7bR)-5,5a,6,7,7a,7b-hexahydro-7b-[(2-(N-pyrrolidinyl)-3-pyridinyl)methoxy]-4-methyl-indeno[1,7-bc]furan-2(4H)-one

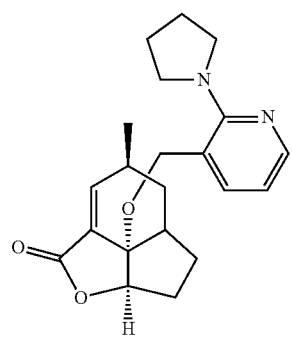 [SMILES: C[C@@H]1C=C2C(=O)O[C@@H]3CCC(C1)[C@]23OCc1cccnc1N1CCCC1]

heptane/EtOAC 9:1. Yield 72%
$^1$H NMR (500 MHz, CDCl$_3$) δ 8.11 (m, 1H), 7.44 (m, 1H), 7.17 (m, 1H), 6.63 (m, 1H), 4.94 (m, 1H), 4.38 (m, 1H), 4.36 (m, 1H), 3.50 (m, 4H), 2.56 (m, 2H), 2.26 (m, 1H), 2.09 (m, 1H), 1.91 (m, 4H), 1.87 (m, 1H), 1.81 (m, 1H), 1.21 (m, 1H), 1.21 (m, 3H), 1.02 (m, 1H).

Example 19

(4R,5aS,7aS,7bR)-5,5a,6,7,7a,7b-hexahydro-7b-[(2-indolinyl)methoxy]-4-methyl-indeno[1,7-bc]furan-2(4H)-one

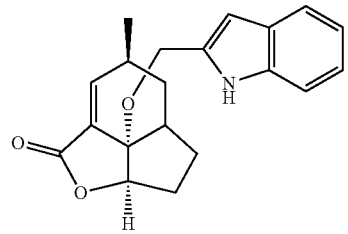 [SMILES: C[C@@H]1C=C2C(=O)O[C@@H]3CCC(C1)[C@]23OCc1cc2ccccc2[nH]1]

heptane/EtOAC 7:3. Yield 64%
$^1$H NMR (500 MHz, CDCl$_3$) δ 8.31 (s, 1H), 7.57 (m, 1H), 7.36 (m, 1H), 7.22 (m, 1H), 7.18 (m, 1H), 7.10 (m, 1H), 4.92 (m, 1H), 4.57 (m, 1H), 4.54 (m, 1H), 2.63 (m, 1H), 2.59 (m, 1H), 2.27 (m, 1H), 2.08 (m, 1H), 1.88 (m, 1H), 1.82 (m, 1H), 1.22 (m, 3H), 1.20 (m, 1H), 1.00 (m, 1H).

Example 20

(4R,5aS,7aS,7bR)-5,5a,6,7,7a,7b-hexahydro-7b-[(2-benzimidazolyl)methoxy]-4-methyl-indeno[1,7-bc]furan-2(4H)-one

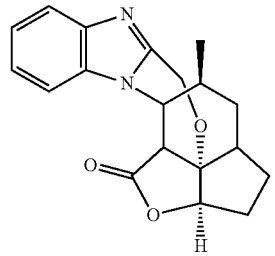 [SMILES: C[C@H]1CC2CC[C@H]3OC(=O)C4C1n1c(nc5ccccc51)CO[C@@]243]

heptane/EtOAc 4:6. Yield 88%.
$^1$H NMR (400 MHz, CDCl$_3$) δ 7.77 (m, 1H), 7.52 (m, 1H), 7.40 (m, 1H), 7.32 (m, 1H), 5.26 (m, 1H), 5.07 (m, 1H), 4.82 (m, 1H), 4.78 (m, 1H), 3.16 (brs, 1H), 2.65 (m, 1H), 2.41 (m, 1H), 2.22 (m, 1H), 2.02 (m, 1H), 2.00 (m, 1H), 1.93 (m, 1H), 1.65 (m, 1H), 1.33 (m, 3H), 0.98 (m, 1H).

Example 21

(4R,5aS,7aS,7bR)-5,5a,6,7,7a,7b-hexahydro-7b-[(2-(5-chloro-benzimidazolyl)methoxy]-4-methyl-indeno[1,7-bc]furan-2(4H)-one

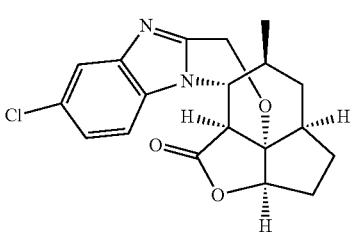 [SMILES: C[C@H]1C[C@H]2CC[C@H]3OC(=O)[C@H]4[C@@H]1n1c(nc5cc(Cl)ccc51)CO[C@]234]

heptane/Et$_2$O 9:1. Yield 45%
$^1$H NMR (500 MHz, CD$_2$Cl$_2$, solvent peak at 5.32 ppm) δ 7.67 (m, 1H), 7.45 (m, 1H), 7.32 (m, 1H), 5.10 (m, 1H), 5.02 (m, 1H), 4.76 (m, 1H), 4.72 (m, 1H), 3.15 (m, 1H), 2.63 (m, 1H), 2.38 (m, 1H), 2.17 (m, 1H), 1.99 (m, 1H), 1.98 (m, 1H), 1.90 (m, 1H), 1.60 (m, 1H), 1.28 (m, 3H), 0.92 (m, 1H).

Example 22

(4R,5aS,7aS,7bR)-5,5a,6,7,7a,7b-hexahydro-7b-[(2-(6-chloro-benzimidazolyl)methoxy]-4-methyl-indeno[1,7-bc]furan-2(4H)-one

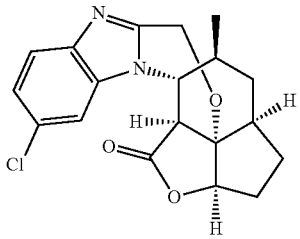 [SMILES: C[C@H]1C[C@H]2CC[C@H]3OC(=O)[C@H]4[C@@H]1n1c(nc5ccc(Cl)cc51)CO[C@]234]

heptane/Et$_2$O 9:1. Yield 40%

$^1$H NMR (500 MHz, CD$_2$Cl$_2$, solvent peak at 5.32 ppm) δ 7.61 (m, 1H), 7.53 (m, 1H), 7.23 (m, 1H), 5.10 (m, 1H), 5.02 (m, 1H), 4.75 (m, 1H), 4.68 (m, 1H), 3.12 (m, 1H), 2.63 (m, 1H), 2.38 (m, 1H), 2.17 (m, 1H), 1.98 (m, 1H), 1.98 (m, 1H), 1.92 (m, 1H), 1.60 (m, 1H), 1.29 (m, 3H), 0.92 (m, 1H).

Example 23

(4R,5aS,7aS,7bR)-5,5a,6,7,7a,7b-hexahydro-7b-[(2-(3H-imidazo[4,5-b]pyridinyl)methoxy]-4-methyl-indeno[1,7-bc]furan-2(4H)-one

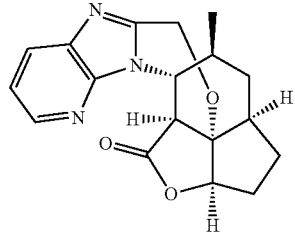 [SMILES: C[C@H]1C[C@H]2CC[C@H]3OC(=O)[C@H]4[C@@H]1n1c(nc5cccnc51)CO[C@]234]

heptane/Et$_2$O 9:1. Yield 55%

$^1$H NMR (500 MHz, CD$_2$Cl$_2$, solvent peak at 5.32 ppm) δ 8.41 (m, 1H), 7.98 (m, 1H), 7.24 (m, 1H), 5.30 (m, 1H), 5.09 (m, 1H), 5.07 (m, 1H), 4.75 (m, 1H), 3.09 (m, 1H), 2.65 (m, 1H), 2.39 (m, 1H), 2.17 (m, 1H), 2.00 (m, 1H), 1.99 (m, 1H), 1.89 (m, 1H), 1.62 (m, 1H), 1.30 (m, 3H), 0.94 (m, 1H).

Example 24

(4R,5aS,7aS,7bR)-5,5a,6,7,7a,7b-hexahydro-7b-[(2-(5-methoxy-benzimidazolyl)methoxy]-4-methyl-indeno[1,7-bc]furan-2(4H)-one

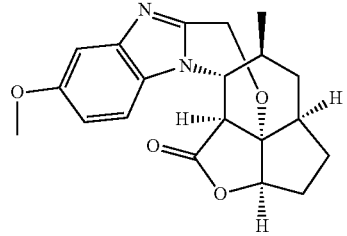 [SMILES: COc1ccc2c(c1)nc1n2[C@@H]2[C@@H](C)C[C@H]3CC[C@H]4OC(=O)[C@@H]2[C@@]34OC1]

heptane/Et$_2$O 9:1. Yield 60%

$^1$H NMR (500 MHz, CDCl$_3$) δ 7.62 (m, 1H), 6.92 (m, 1H), 6.91 (m, 1H), 5.12 (m, 1H), 5.02 (m, 1H), 4.78 (m, 1H), 4.70 (m, 1H), 3.91 (s, 3H), 3.14 (m, 1H), 2.64 (m, 1H), 2.40 (m, 1H), 2.21 (m, 1H), 2.01 (m, 1H), 2.00 (m, 1H), 1.94 (m, 1H), 1.64 (m, 1H), 1.33 (m, 3H), 0.96 (m, 1H).

Example 25

(4R,5aS,7aS,7bR)-5,5a,6,7,7a,7b-hexahydro-7b-[(2-(N-morpholino)-5-(1,3-thiazolyl))methoxy]-4-methyl-indeno[1,7-bc]furan-2(4H)-one

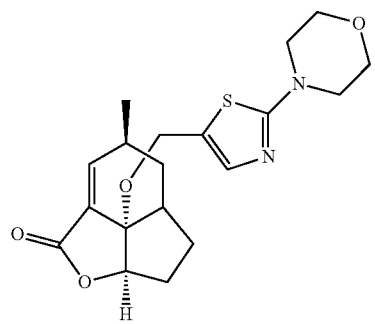 [SMILES: C[C@@H]1C=C2C(=O)O[C@@H]3CCC(C1)[C@]23OCc1cnc(N2CCOCC2)s1]

heptane/EtOAC 4:6. Yield 80%

$^1$H NMR (500 MHz, CDCl$_3$) δ 7.19 (m, 1H), 7.03 (s, 1H), 4.91 (m, 1H), 4.40 (s, 3H), 3.79 (m, 4H), 3.43 (m, 4H), 2.60 (m, 1H), 2.52 (m, 1H), 2.24 (m, 1H), 2.06 (m, 1H), 1.84 (m, 1H), 1.82 (m, 1H), 1.21 (m, 3H), 1.14 (m, 1H), 0.94 (m, 1H).

Synthesis of 4α-Fluoro-galiellalactone Acetate from Galiellalactone (Scheme 5)

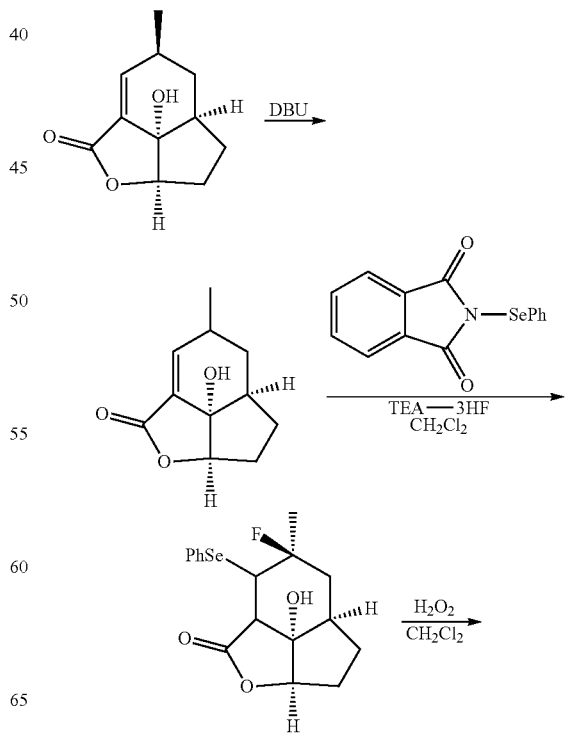

51
-continued

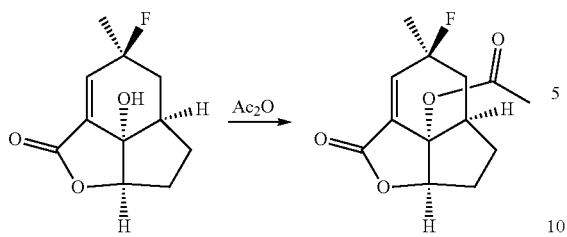

Iso-Galiellalactone

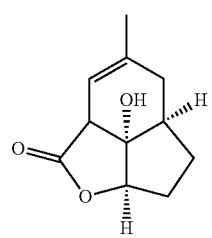

1.6 g (10.30 mmol) 1,8-Diazabicyclo[5.4.0]undec-7-ene (DBU) was added to a solution of 500 mg (2.57 mmol) galiellalactone in $CH_2Cl_2$ and stirred overnight at room temperature. Purification with flash chromatography (heptane/EtOAc 7:3), afforded 450 mg of iso-galiellalactone. (90%)

$^1$H NMR (CDCl$_3$) δ 5.05 (m, 1H), 4.78 (m, 1H), 3.19 (s, 1H), 2.85 (m, 1H), 2.37 (m, 1H), 2.21 (m, 1H), 1.95 (m, 1H), 1.90 (m, 1H), 1.90 (m, 1H), 1.76 (s, 1H), 1.65 (m, 1H), 1.42 (m, 1H).

4α-Fluoro-galiellalactone

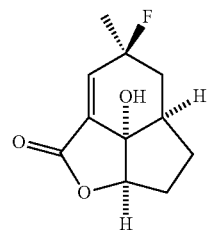

Iso-galiellalactone was dissolved in $CH_2Cl_2$ and 1.5 mmol (1.5 eq) N-phenyl selenyl phthalimide was added followed by 6 mmol (6 eq) TEA-3HF. The reaction mixture was stirred at room temperature overnight diluted with diethyl ether and washed with $NaHCO_3$ (aq). The organic phase was dried and concentrated under reduced pressure.

To a solution of resulting crude selenylated product (38 mg, 0.1 mmol) in 2 ml of $CH_2Cl_2$ was added $H_2O_2$ (12 uL) at 0° C. under $N_2$, and stirred for 3 h. The reaction was quenched by 2 ml $NaHCO_3$ sat at 0° C. and extracted with $CH_2Cl_2$ (5 ml×3), dried with $MgSO_4$ and concentrated under reduced pressure. Purification with flash chromatography (heptane/EtOAc 7:3), afforded 16 mg of the 4α-fluoro-galiellalactone. (65%)

$^1$H NMR (CDCl$_3$) δ 6.91 (d, 1H), 4.86 (d, 1H), 2.42 (m, 1H), 2.29 (m, 1H), 2.19 (m, 1H), 2.14 (m, 1H), 1.80 (m, 1H), 1.75 (m, 1H), 1.61 (d, 3H), 1.60 (m, 1H)

52
4α-Fluoro-galiellalactone Acetate

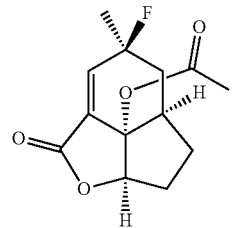 [SMILES: CC(=O)O[C@]12C3=C[C@@](C)(F)C[C@H]1CC[C@H]2OC3=O]

4α-fluoro-galiellalactone acetate was prepared from 4α-fluoro-galiellalactone using the acetylation procedure described in "Biosynthetic and Synthetic Studies of the Fungal Metabolite Galiellalactone", Martin Johansson, Doctoral Thesis, Lund University 2002 and in "The High-Intrinsic Diels-Alder Reactivity of (−)-Galiellalactone; Generating Four Quaternary Carbon Centers under Mild Conditions" Franz von Nussbaum, Roman Hanke, Thomas Fahrig, Jordi Benet-Buchholz, *Eur. J. Org. Chem.* 13, 2783-2790 (2004).

Example 26 was prepared from 4α-fluoro-galiellalactone acetate and the corresponding alcohol (III) following the general procedure for the synthesis of galiellalactone ethers 7b described above in scheme 4.

Example 26

(4R,5aS,7aS,7bR)-5,5a,6,7,7a,7b-hexahydro-7b-[(6-methyl-3-pyridinyl)methoxy]-4-fluoro-4-methyl-indeno[1,7-bc]furan-2(4H)-one

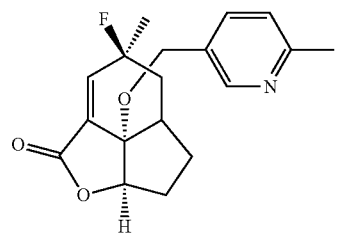 [SMILES: Cc1ccc(CO[C@]23C4=C[C@@](C)(F)CC2CC[C@H]3OC4=O)cn1]

100% EtOAc. Yield 70%
$^1$H NMR (500 MHz, CDCl$_3$) δ 8.40 (m, 1H), 7.47 (m, 1H), 7.15 (m, 1H), 7.10 (m, 1H), 5.04 (m, 1H), 4.46 (m, 1H), 4.40 (m, 1H), 2.52 (m, 1H), 2.51 (m, 1H), 2.27 (m, 1H), 2.12 (m, 1H), 1.89 (m, 1H), 1.82 (m, 1H), 1.58 (m, 3H), 1.56 (m, 1H).

Example 27

(4R,5aS,7aS,7bR)-5,5a,6,7,7a,7b-hexahydro-7b-[2-(3-pyridinyl)-ethoxy]-4-fluoro-4-methyl-indeno[1,7-bc]furan-2(4H)-one

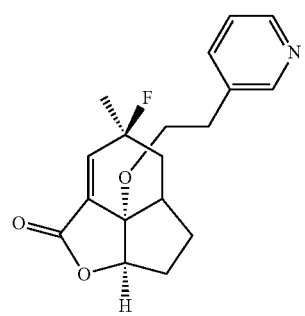 [SMILES: C[C@@]1(F)C=C2C(=O)O[C@@H]3CCC(C1)[C@]23OCCc1cccnc1]

$^1$H NMR (500 MHz, CDCl$_3$) δ 8.46 (m, 1H), 8.43 (m, 1H), 7.49 (m, 1H), 7.21 (m, 1H), 6.96 (s, 1H), 4.84 (m, 1H), 3.66 (m, 1H), 3.52 (m, 1H), 2.82 (m, 2H), 2.38 (m, 1H), 2.07 (m, 1H), 2.05 (m, 1H), 2.00 (m, 1H), 1.75 (m, 1H), 1.74 (m, 1H), 1.49 (m, 1H), 1.32 (s, 3H).

Example 28

(4R,5aS,7aS,7bR)-5,5a,6,7,7a,7b-hexahydro-7b-[(6-(N-morpholino)-3-pyridinyl)methoxy]-4-fluoro-methyl-indeno[1,7-bc]furan-2(4H)-one

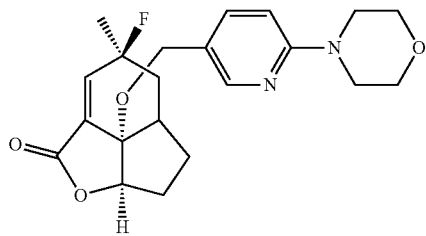 [SMILES: C[C@@]1(F)C=C2C(=O)O[C@@H]3CCC(C1)[C@]23OCc1ccc(N2CCOCC2)nc1]

$^1$H NMR (500 MHz, CDCl$_3$) δ 8.08 (m, 1H), 7.39 (m, 1H), 7.09 (s, 1H), 6.61 (m, 1H), 5.04 (m, 1H), 4.34 (m, 1H), 4.30 (m, 1H), 3.82 (m, 4H), 3.50 (m, 4H), 2.48 (m, 1H), 2.26 (m, 1H), 2.14 (m, 1H), 2.10 (m, 1H), 1.82 (m, 1H), 1.79 (m, 1H), 1.59 (s, 3H), 1.54 (m, 1H).

Comparative Pharmacokinetic Study of Galiellalactone and Example 20

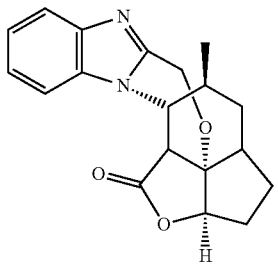

Example 20

A pharmacokinetic study was performed in CD1 mice to establish plasma exposure following administration of single oral doses of galiellalactone and example 20. Sample analysis was by LC-MS/MS.

Dose solutions were prepared at a drug concentration of 0.5 mg/mL in 5% DMSO in 50 mM citrate buffer (citric acid/sodium citrate pH 4.0) and administered as a 20 mL/kg oral gavage (10 mg/kg).

The measured concentrations of galiellalactone and example 20 are shown in Table 1. AUC denotes the plasma exposure of the compound measured with time. More specifically, AUC 0-t is the area under the plasma drug concentration/time curve from 0 minutes to last quantifiable data point. AUC 0-∞ is the area under the plasma drug concentration/time curve from 0 minutes extrapolated to infinity.

TABLE 1

Measured Pharmacokinetic Parameters

| Pharmacokinetic Parameter | Galiellalactone | Example 20 |
|---|---|---|
| $C_{max}$ (ng/mL) | 52 | 530 |
| $T_{max}$ (h) | 0.5 | 0.25 |
| Apparent half-life (h) | 1.2 | 1.5 |
| AUC 0-t (ng/mL · h) | 82 | 622 |
| AUC 0-∞ (ng/mL · h) | 87 | 634 |

The pharmacokinetic study shows that following oral administration at 10 mg/kg quantifiable concentrations were detected in at least one animal from each time point out to the final 8 hour samples. $T_{max}$ was the first time point in all cases suggesting rapid absorption from the gut. As can be seen by the values of AUC 0-t and AUC 0-∞, a higher exposure was measured for example 20 compared to galiellalactone, suggesting lower clearance, lower volume and improved bioavailability of example 20.

Biological Examples

Biological Example

Selected example compounds were evaluated in vitro in cellular assays.

Anti-proliferative Activity of Example Compounds

WST-1 Cell Proliferation Assay

The functional activity of the example compounds in comparison to galiellalactone was evaluated using a WST-1 proliferation assay (J. Biol. Chem. 2014, 289:15969-15978) on DU145, LNCaP or IL-6 stimulated LNCaP.

| Cell type | pSTAT3 expression |
|---|---|
| DU145 | + |
| LNCaP | − |
| LNCaP-IL6 | + |

The cells were cultured in 96-well plates (2000 cells/well in 200 µl of medium) and allowed to set for 24 h. The cells were treated with 10 µM of an example compound or galiellalactone for 72 h. Samples were made in triplicate. 20 µl WST-1 solution (Roche Applied Science) was added per well and incubated at 37° C. for 4 h. The absorbance of each well was measured using a scanning multi-well spectrophotometer, ELISA reader at a wavelength of 450 nm and reference wavelength of 690 nm. The results presented in Tables 2 and 3 below are presented as percent of untreated control cells.

TABLE 2

Proliferation of pSTAT3 cell lines in the presence of galiellalactone and selected examples at 10 µM.

| | Remaining cell proliferation (%) | | | Difference in cell proliferation @ 10 µM (%) (Selectivity) | |
|---|---|---|---|---|---|
| Example No. | DU145 | LNCaP | LNCaP-IL6 | Δ LNCaP − DU145 | Δ LNCaP − LNCaPIL6 |
| Galiellalactone | 10.8 | 43.6 | 4.7 | 32.8 | 38.9 |
| 1 | 12.9 | 63.2 | 8.6 | 50.3 | 54.6 |
| 2 | 36.1 | 86.0 | 18.0 | 49.9 | 68 |
| 3 | 18.7 | 68.6 | 8.0 | 49.9 | 60.6 |
| 4 | 11.4 | 55.5 | 10.7 | 44.1 | 44.8 |
| 5 | 19.0 | 86.0 | 15.0 | 67 | 71 |

TABLE 2-continued

Proliferation of pSTAT3 cell lines in the presence of galiellalactone and selected examples at 10 μM.

| | Remaining cell proliferation (%) | | | Difference in cell proliferation @ 10 μM (%) (Selectivity) | |
|---|---|---|---|---|---|
| Example No. | DU145 | LNCaP | LNCaP-IL6 | Δ LNCaP – DU145 | Δ LNCaP – LNCaPIL6 |
| 6 | 16.6 | 65.6 | 15.9 | 49 | 49.7 |
| 7 | 16.7 | 59.3 | 7.0 | 42.6 | 52.3 |
| 8 | 10.0 | 54.5 | 3.0 | 44.5 | 51.5 |
| 9 | 9.7 | 67.6 | 2.8 | 57.9 | 64.8 |
| 15 | 9.6 | 76.1 | 6.5 | 66.6 | 69.6 |

DU145 and LNCaPIL6 are STAT3 driven cell lines, whereas LNCaP is a non-STAT3 driven cell line. As can be seen in Table 2, all tested ether analogues were anti-proliferative. Whereas the anti-proliferative effect of ether analogues on the STAT3 driven cell lines was similar to one seen with galiellalactone, the ether analogues were all less effective in providing anti-proliferative effects on the non-STAT3 driven cell line. Thus, indicating the ether analogues displays higher selectivity for STAT3.

In order to further asses the properties of the ether analogues of galiellalactone, the STAT1 activity was determined for some of the novel analogues.

TABLE 3

Inhibition of STAT1 as measured in a reporter gene assay. Briefly, HeLa cells were transfected with 100 ng of a luciferase reporter plasmids and stimulated with IFNg overnight.

| Example No. | STAT1 inhibition at 10 μM |
|---|---|
| Galiellalactone | 62% |
| 1 | 14% |
| 2 | 1% |
| 3 | 38% |
| 4 | 12% |
| 5 | 16% |
| 15 | 53% |

It was found that all tested examples (cf. Table 3) have decreased ability to inhibit STAT1 compared to galiellalactone. This finding is coherent with the data in table 2 and further supports the novel ether analogues being more selective for STAT3 than galiellalactone.

Thus an embodiment relates to compounds and pharmaceutical compositions disclosed herein, e.g. compounds according to formula (I) or formula (II) or preferred selections thereof, for inhibiting the activity of a STAT3 receptor to a larger extent than the compound or composition inhibits the activity of a STAT1 receptor.

Compounds wherein $R_1$ is fluorine have been found to be of particular interest, as the presence of fluorine seemingly increases the activity. As can be seen in Table 4 below, example 26 ($R_1$=fluorine; $R_1'$=hydrogen) provided a compound with lower IC50 value than the parent compound galiellelactone. Compounds wherein $R_1$ is fluorine are thus preferred according to some embodiments. In such embodiments, $R_1'$ is typically methyl.

TABLE 4

Cell proliferation IC50 values as determined by performing a dose response study using the prosatate cancer cell lines DU145 and LNCaPIL6.

| | IC50 (μM) | |
|---|---|---|
| Example No. | DU145 | LNCaP-IL6 |
| Galiellalactone | 2.52 | 1.16 |
| 26 | 1.53 | 1.06 |

Figure 1B:
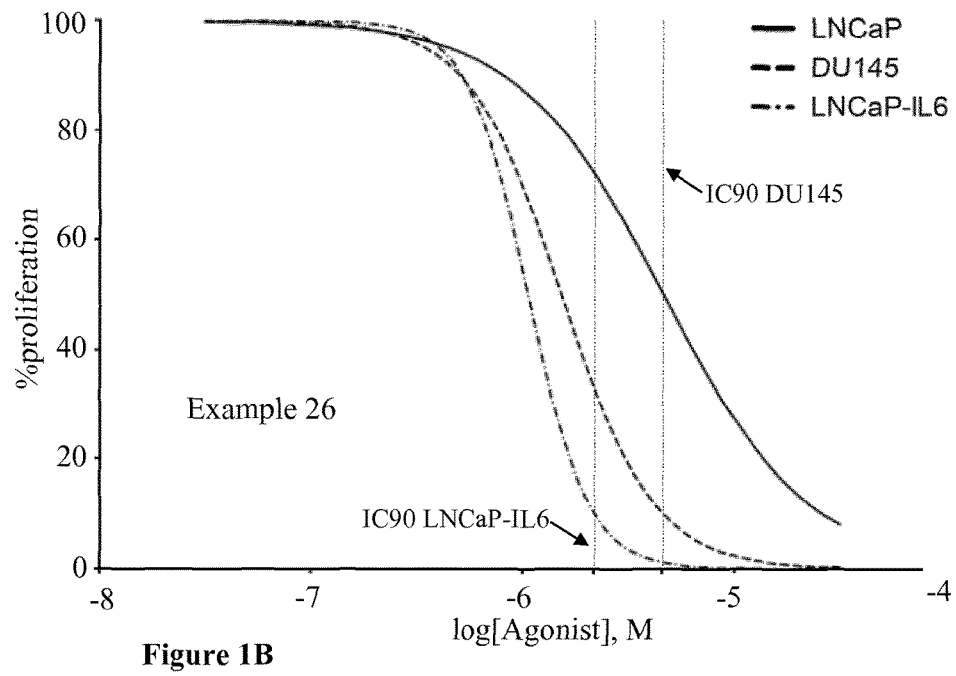

FIGS. 1A and 1B show the dose response curves for galiellalactone and example 26 for the inhibition of proliferation of DU145, LNCaP-IL6 and LNCaP cells. As can be seen in FIG. 1B, example 26 shows very good selectivity at the respective IC90 values against DU145 and LNCap-IL6 cell proliferation over LNCaP proliferation. The selectivity is improved compared to galiellalactone as seen in FIG. 1A. The selectivity at IC90 (μM)) is measured as near complete inhibition of cell proliferation is desired. FIGS. 1A and 1B also demonstrate the potency of example 26 compared to galiellalactone at inhibiting STAT3 as measured in the STAT3 driven cell lines (DU145 and LNCaPIL6) and a non-STAT3 driven cell line (LNCaP).

Western Blot Analysis of pSTAT3 in Prostate Cancer Cells

Samples were separated on 7.5% precast gel (Mini-PROTEAN TGX; Bio-Rad) or 8% Tris Bis self cast gels. The gels were blotted onto PVDF membranes and blocked with 5% milk or 5% BSA. Membranes were incubated with primary antibody diluted in 5% milk or 5% BSA for 1 h at room temperature or over night at 4° C. with antibodies raised against STAT3 and pSTAT3 tyr-705 (Cell Signaling Technology). After incubation with secondary anti-mouse or anti-rabbit antibody conjugated with horseradish peroxidase (GE Healthcare Life Sciences) the membrane was treated with enhanced chemiluminescent reagent (Santa Cruz Biotechnology or Millipore) followed by exposure to X-Ray film or visualized using a Chemidoc XRS system (Bio-Rad).

Figure 2:
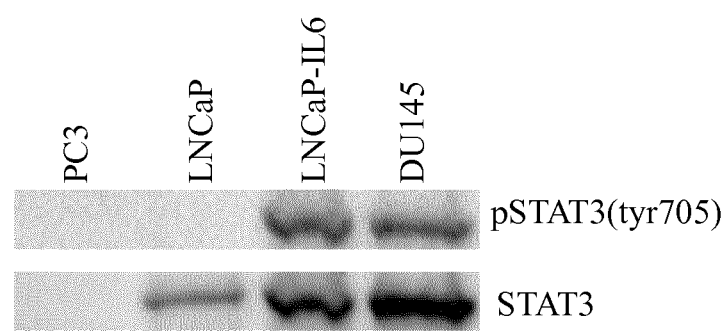

FIG. 2 shows an image of the Western blot analysis of p-STAT3(tyr705) and total STAT3 in DU145, LNCaP-IL6 LNCaP and PC-3 prostate cancer cell lines.

As shown in FIG. 2, only DU145 and LNCaP-IL6 cells express active pSTAT3. This shows that DU145 and LNCaPIL6 are STAT3 driven cell lines whereas LNCaP is a non-STAT3 driven cell line as pSTAT3 is a driver of proliferation.

The invention claimed is:

1. A compound according to formula (I)

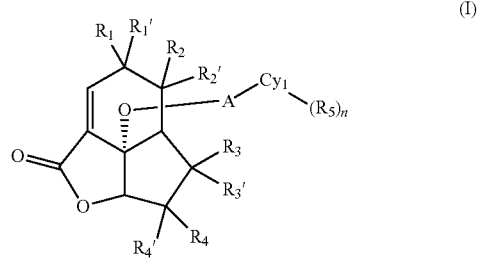

wherein $R_1$ and $R_1'$ are independently selected from the group consisting of H, C1-5 alkyl, C1-5 fluoroalkyl, halo, cyano, nitro, —OH, OC1-5 alkyl, C1-5 alkyleneOH, C1-5 alkyleneOC1-5 alkyl, C3-8 non-aromatic carbocycle, OC1-5 fluoroalkyl, C1-3 alkyleneOC1-5 fluoroalkyl, OC(O)C1-5 alkyl, C1-3 alkyleneOC(O)C1-5 alkyl, OC2-3 alkyleneNH$_2$, OC2-3 alkyleneNH(C1-5 alkyl), OC2-3 alkyleneN(C1-5 alkyl)$_2$ in which the C1-5 alkyl are the same or different, —NH$_2$, —NH(C1-5 alkyl), C1-3 alkyleneNH$_2$, C1-3 alkyleneNH(C1-5 alkyl), —N(C1-5 alkyl)$_2$ in which the C1-5 alkyl are the same or different, C1-3 alkyleneN(C1-5 alkyl)$_2$ in which the C1-5 alkyl are the same or different, NHC(O)C1-5 alkyl, N(C1-5 alkyl)C(O)C1-5 alkyl, C1-3 alkyleneNHC(O)C1-5 alkyl, C1-3 alkyleneN(C1-5 alkyl)C(O)C1-5 alkyl, NHaryl, C1-3 alkyleneNHaryl, wherein the aryl is unsubstituted or substituted with one or more substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, NH2, NH(C1-5 alkyl), and N(C1-5 alkyl)$_2$ in which the C1-5 alkyl are the same or different, aryl, C1-3 alkylene-aryl, wherein the aryl is unsubstituted or substituted with one or several substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, —NH$_2$, —NH(C1-5 alkyl), and N(C1-5 alkyl)$_2$ in which the C1-5 alkyl are the same or different, —SH, —SC1-5 alkyl, C1-5 alkylene-SH, C1-5 alkylene-SC1-5 alkyl, SC1-5 fluoroalkyl, C1-5 alkyleneSC1-5 fluoroalkyl, SO2C1-5 alkyl, C1-5 alkylene-SO2C1-5 alkyl, SO2C1-5 fluoroalkyl, C1-5 alkylene-SO2C1-5 fluoroalkyl, SO$_2$NH$_2$, SO$_2$NH(C1-5 alkyl), SO$_2$N(C1-5 alkyl)$_2$ in which the C1-5 alkyl are the same or different, C1-5 alkyleneSO$_2$NH$_2$, C1-5 alkyleneSO$_2$NH(C1-5 alkyl), C1-5 alkyleneSO$_2$N(C1-5 alkyl)$_2$ in which the C1-5 alkyl are the same or different, SO2NHaryl, C1-5 alkyleneSO2NHaryl, wherein the aryl is unsubstituted or substituted with a one or several substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, —NH$_2$, —NH(C1-5 alkyl), and N(C1-5 alkyl)$_2$ in which the C1-5 alkyl are the same or different, SO2N(C1-5 alkyl)aryl, and C1-5 alkyleneSO2N(C1-5 alkyl)aryl, wherein the aryl is unsubstituted or substituted with a one or several substituents independently selected from the group consisting of C1-5 alkyl, C1-5 fluoroalkyl, halo, —OH, OC1-5 alkyl, C1-5 alkyleneOH, C1-5 alkyleneOC1-5 alkyl, nitro, cyano, —NH$_2$, —NH(C1-5 alkyl), and N(C1-5 alkyl)$_2$ in which the C1-5 alkyl are the same or different;

$R_2$, $R_2'$, $R_3$, and $R_3'$ are each independently selected from the group consisting of H, halo, —OH, C1-5 alkyl, and C1-5 fluoroalkyl;

$R_4$ and $R_4'$ are independently selected from the group consisting of H, C1-5 alkyl, aryl, and CH$_2$aryl;

A is selected from the group consisting of a bond, C1-5 alkylene or $NR_{10}$;

$R_{10}$ is H or C1-C3 alkyl;

$Cy_1$ is pyridinyl;

$R_5$ is independently selected from the group consisting of C1-8 alkyl, C1-5 haloalkyl, halo, cyano, —CH$_2$-cyano, —OH, OC1-5 alkyl, C1-8 alkyleneOC1-5 alkyl, O-aryl, C1-8 alkylene-O-aryl, —SH, SC1-5 alkyl, SO$_2$H, SO$_2$C1-5 alkyl, C1-3 alkyleneSO$_2$H, C1-3 alkyleneSO$_2$C1-5 alkyl, OC1-3 fluroalkyl, C1-3 alkyleneOC1-3 fluroalkyl, NH2, NH(C1-3 alkyl), C1-3 alkylene-NH2, C1-3 alkyleneNH(C1-3 alkyl), N(C1-5 alkyl)$_2$ in which the C1-5 alkyl are the same or different, C1-3 alkyleneN(C1-5 alkyl)$_2$ in which the C1-5 alkyl are the same or different, C(O)OH, C(O)OC1-5 alkyl, C1-3 alkyleneC(O)OH, C1-3 alkyleneC(O)OC1-5 alkyl, OC(O)H, OC(O)C1-5 alkyl, C1-3 alkyleneOC(O)H, C1-3 alkyleneOC(O)C1-5 alkyl, NHC(O)H, NHC(O)C1-5 alkyl, N(C1-3 alkyl)C(O)H, N(C1-3 alkyl)C(O)C1-5 alkyl, C1-3 alkyleneNHC(O)H, C1-3 alkyleneNHC(O)C1-5 alkyl, C1-3 alkyleneN(C1-3 alkyl)C(O)H, C1-3 alkyleneN(C1-3 alkyl)C(O)C1-5 alkyl, C(O)NH2, C(O)NH(C1-3 alkyl), C1-3 alkyleneC(O)NH2, C1-3 alkyleneC(O)NH(C1-3 alkyl), C(O)N(C1-5 alkyl)$_2$, in which the C1-5 alkyl are the same or different, C1-3 alkyleneC(O)N(C1-5 alkyl)$_2$, in which the C1-5 alkyl are the same or different, nitro, C(O)H, C(O)C1-C5 alkyl, NHSO2C1-C3 alkyl, N(C1-C3 alkyl)SO2C1-C3 alkyl, NHSO2C1-C3 fluoroalkyl, N(C1-C3 alkyl)SO2C1-C3 fluoroalkyl, OC2-C3alkyleneNH2, OC2-C3alkyleneNH(C1-C3 alkyl), OC2-C3alkyleneN(C1-C3 alkyl)$_2$ in which the C1-3 alkyl are the same or different, and

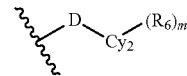

wherein

D is selected from the group consisting of a bond, C1-3 alkylene, O—C1-3 alkylene, C1-3 alkylene-O—C1-3 alkylene, OC(O)C1-3 alkylene, C1-3 alkylene-OC(O)-C1-3 alkylene, C(O)OC1-3 alkylene, C1-3 alkylene-C(O)O—C1-3 alkylene, C(O)N(H)(C1-3 alkylene), C(O)N(C1-3 alkyl)(C1-3 alkylene), C1-3 alkylene-C(O)N(H)(C1-3 alkylene), C1-3 alkylene-C(O)N(C1-3 alkyl)(C1-3 alkylene), N(H)C(O)C1-3 alkylene, N(C1-3 alkyl)C(O)C1-3 alkylene, C1-3 alkylene-N(H)C(O)C1-3 alkylene, C1-3 alkylene-N(C1-3 alkyl)C(O)C1-3 alkylene, —NHSO2-, —SO2NH—, SO2, SO, C(O), C1-3 alkylene-C(O), C(O)C1-3 alkylene, C1-3 alkylene C(O)C1-3 alkylene, NH, N(C1-3 alkyl), NH-C1-3 alkylene, N(C1-3 alkyl)-C1-3 alkylene, C1-3 alkylene-NH, C1-3 alkylene-N(C1-3 alkyl), C1-3 alkylene-NH-C1-3 alkylene, C1-3 alkylene-N(C1-3 alkyl)-C1-3 alkylene, and S;

Cy$_2$ is a phenyl, or a C3-8 non-aromatic carbocycle;

m is an integer selected from the group consisting of 0, 1, 2, 3, 4, and 5;

$R_6$ is independently selected from oxo, C1-5 alkyl, C1-5 fluoroalkyl, halo, cyano, —CH$_2$-cyano, —OH, OC1-5 alkyl, C1-5 alkylene-OH, C1-5 alkyleneOC1-5 alkyl, —SH, SC1-5 alkyl, SO2H, SO2C1-5 alkyl, C1-3 alkyleneSO2H, C1-3 alkyleneSO2C1-5 alkyl, OC1-3 fluoroalkyl, C1-3 alkyleneOC1-3 fluoroalkyl, NH2, NH(C1-3 alkyl), C1-3 alkylene-NH2, C1-3 alkylene-NH(C1-3 alkyl), N(C1-5 alkyl)2 in which the C1-5 alkyl are the same or different, C1-3 alkyleneN(C1-5 alkyl)2 in which the C1-5 alkyl are the same or different, C(O)OH, C(O)OC1-5 alkyl, C1-3 alkylene-C(O)OH, C1-3 alkylene-C(O)OC1-5 alkyl, OC(O)H, OC(O)C1-5 alkyl, C1-3 alkylene-OC(O)H, C1-3 alkylene-OC(O)C1-5 alkyl, NHC(O)H, NHC(O)C1-3 alkyl, N(C1-3 alkyl)C(O)H, N(C1-3 alkyl)C(O)C1-3 alkyl, C1-3 alkylene-NHC(O)H, C1-3 alkylene-NHC(O)C1-3 alkyl, C1-3 alkylene-N(C1-3 alkyl)C(O)H, C1-3 alkylene-N(C1-3 alkyl)C(O)C1-3 alkyl, C(O)NH2, C(O)NH(C1-3 alkyl), C1-3 alkylene-C(O)NH2, C1-3 alkylene-C(O)NH(C1-3 alkyl), C(O)N(C1-5 alkyl)2 in which the C1-5 alkyl are the same or different, C1-3 alkyleneC(O)N(C1-5 alkyl)2 in which the C1-5 alkyl are the same or different, C(O)N(C4-5 alkylene), C1-3 alkyleneC(O)N(C4-5 alkylene), nitro, C(O)H, C(O)C1-C5 alkyl, C(O)C1-C3 fluoroalkyl, NHSO$_2$C1-C3 alkyl, N(C1-C3 alkyl)SO$_2$C1-C3 alkyl, NHSO$_2$C1-C3 fluoroalkyl, N(C1-C3 alkyl)SO$_2$C1-C3 fluoroalkyl, OC2-C3alkyleneNH$_2$, OC2-C3alkyleneNH(C1-C3 alkyl), and OC2-C3alkyleneN(C1-C3 alkyl)2 in which the C1-3 alkyl are the same or different; or when two R6 are present, each R6 is combined to form a fused ring or spiro ring with Cy2;

n is an integer selected from the group consisting of 0, 1, and 2;

as a free base, an acid in its non-charged protonated form, a pharmaceutically acceptable addition salt, a pure diastereomer, a pure enantiomer, a diastereomeric mixture, a racemic mixture, a scalemic mixture, a corresponding tautomeric form resulting from a hydrogen shift between two hetero-atoms and/or the corresponding tautomeric form resulting from a keto-enol tautomerization.

2. The compound according to claim 1, wherein A is selected from the group consisting of —CH$_2$—, —CH$_2$CH$_2$—, and —CH$_2$CH$_2$CH$_2$—.

3. The compound according to claim 1, wherein R$_5$ is selected from the group consisting of C1-C4 alkyl, C1-C4 haloalkyl, —OH, C1-C4 alkoxy, C1-C4 alkylamino, (C1-C4 alkyl)$_2$-amino, aryl, aryl aryloxy, heteroaryloxy, C1-C4 alkyl-C(O)—, C1-C4 alkyl-C(O)O—, C1-C4 alkyl-O(O)C—, C1-C4 alkyl-C(O)NH—, C1-C4 alkyl-NH(O)C—, C1-C4 alkyl-C(O)N(C1-C3 alkyl)-, C1-C4 alkyl-N(C1-C3 alkyl)(O)C—, halogen, nitro, and cyano.

4. The compound according to claim 1, wherein R$_5$ is selected from the group consisting of methyl, methoxy, —NH$_2$, fluorine, CF$_3$, —NH(CO)C(CH$_3$)$_3$, phenoxy, acetyl, CH$_3$—C(O)O—, and CH$_3$—O(O)C.

5. The compound according to claim 1, wherein n is 0 or 1.

6. The compound according to claim 1, wherein R$_1$ and R$_1$' are independently selected from the group consisting of hydrogen, C1-C5 alkyl, methyl, C1-5 fluoroalkyl, —OH, C1-C5 alkoxy, methoxy, fluorine, and halogen.

7. The compound according to claim 1, wherein R$_2$, R$_2$', R$_3$, and R$_3$' are all hydrogen; and/or wherein R$_4$ and R$_4$' are both hydrogen.

8. The compound according to claim 1, wherein said compound is selected from the group consisting of:

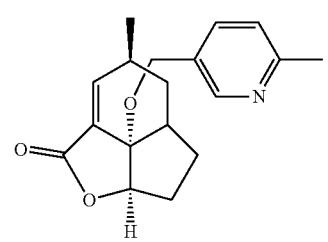

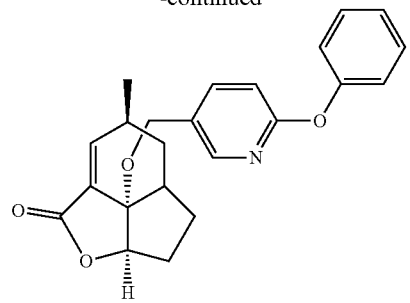

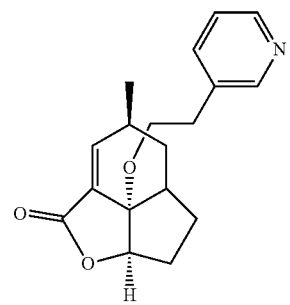

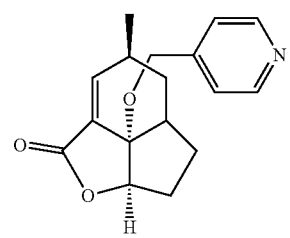

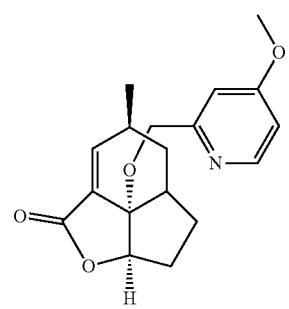

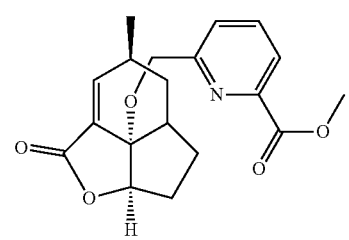

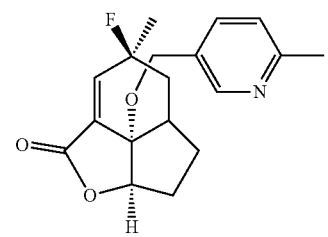

-continued
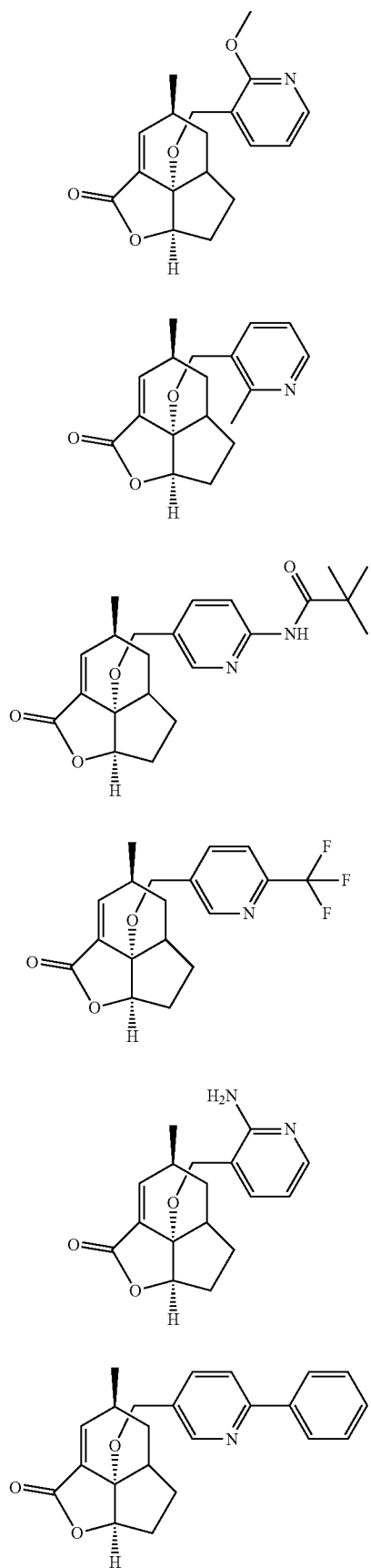
-continued
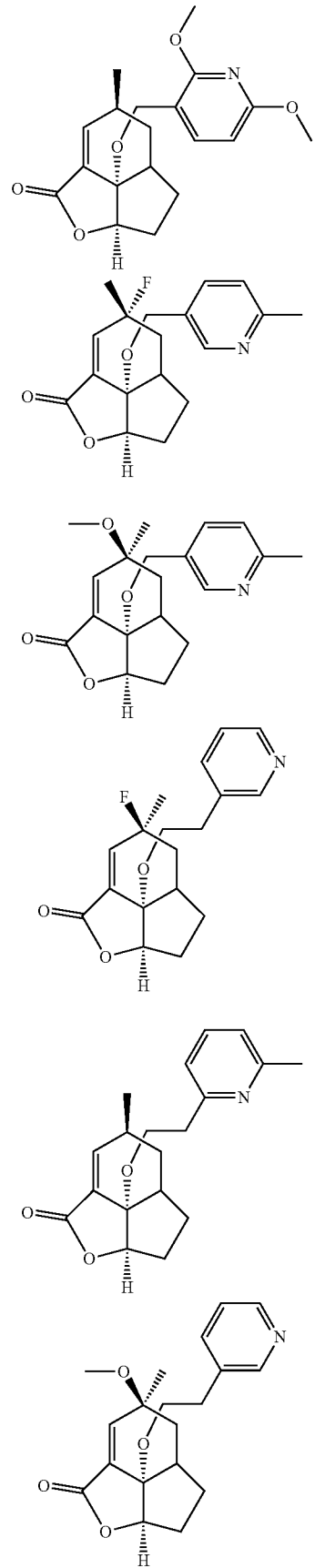

-continued
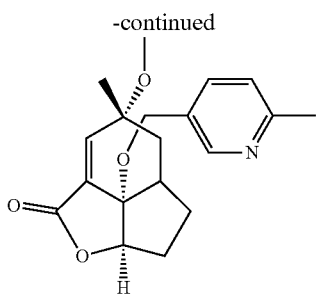
wherein the indicated stereochemistry is relative or absolute stereochemistry.
9. A pharmaceutical composition comprising a compound according to claim 1 and at least one pharmaceutically acceptable carrier or excipient.
* * * * *